United States Patent
Maliga et al.

(10) Patent No.: US 6,472,586 B1
(45) Date of Patent: Oct. 29, 2002

(54) NUCLEAR-ENCODED TRANSCRIPTION SYSTEM IN PLASTIDS OF HIGHER PLANTS

(75) Inventors: Pal Maliga, East Brunswick; Lori A. Allison, Highland Park; Peter T. Hajdukiewicz, Somerset, all of NJ (US)

(73) Assignee: Rutgers, The State University of New Jersey, Piscataway, NJ (US)

( * ) Notice: Subject to any disclaimer, the term of this patent is extended or adjusted under 35 U.S.C. 154(b) by 0 days.

(21) Appl. No.: 09/011,336

(22) PCT Filed: Aug. 1, 1996

(86) PCT No.: PCT/US96/12671

§ 371 (c)(1),
(2), (4) Date: Feb. 10, 1998

(87) PCT Pub. No.: WO97/06250

PCT Pub. Date: Feb. 20, 1997

Related U.S. Application Data

(60) Provisional application No. 60/002,136, filed on Aug. 10, 1995.

(51) Int. Cl.$^7$ .............................. A01H 5/00; C12N 5/04; C12N 15/82
(52) U.S. Cl. ........................ 800/287; 800/278; 800/298; 435/320.1; 435/419; 435/430; 435/468; 536/24.1
(58) Field of Search .............................. 435/320.1, 410, 435/419, 418, 430; 536/24.1, 23.6; 800/298, 300, 278, 287, 288

(56) References Cited

U.S. PATENT DOCUMENTS

| | | | |
|---|---|---|---|
| 5,451,513 A | | 9/1995 | Maliga et al. |
| 5,576,198 A | * | 11/1996 | McBride et al. ............ 435/91.3 |
| 5,877,402 A | * | 3/1999 | Maliga et al. .............. 800/205 |

OTHER PUBLICATIONS

Shinozaki et al, 1986. Intron in the gene for the ribosomal protein S16 of tobacco chloroplast and its conserved boundary sequences. Mol. Gene. Genet. 202:1–5.*
Zoubenko, O. V. et al., "Efficient targeting of foreign genes into the tobacco plastid genome. " 1994, Nucleic Acids Research, vol. 22, pp. 3819–3824.*
Staub et al., "Long Regions of Homologous DNA Are Incorporated into the Tobacco Plastic Genome by Transformation"; The Plant Cell, Jan. 1992, vol. 4, pp. 39–45.
Mullet, John E., "Dynamic Regulation of Chloroplast Transcription"; Plant Physiol. 1993, vol. 103, pp. 309–313.
Tonkyn et al., "Differential expression of the partially duplicated chloroplast S10 ribosomal protein operon"; Mol. Gen. Genet. 1993, vol. 241, pp. 141–142 and 148–152.
Svab et al., "High–frequency plastid transformation in tobacco by selection for a chimeric aadA gene"; Proc. Natl. Acad. Sci. USA, Feb. 1993, vol. 90, pp. 913–917.

Antonio Vera et al., "Chloroplast of rRNA transcription from structurally different tandem promoters: an additional novel– type promoter", Curr Genet (1995) 27:280–284.
Uwe Klein et al., "Two types of chloroplast gene promoters in *Chlamydomonas reinhardtii*"; Proc. Natl. Acad. Sci. USA, vol. 89, pp. 3453–3457, Apr. 1992.
Michael C. Little et al., "Chloroplast rpoA, rpoB, and rpoC Genes Specify at Least Three Components of a Chloroplast DNA–dependent RNA Polymerase Active in tRNA and mRNA Transcription"; The Journal of Biological Chemistry, vol. 263 No. 28, Issue of Oct. 5, pp. 14302–14307, 1988.
Silva Lerbs–Mache, "The 110–kDa polypeptide of spinach plastid DNA–dependent RNA polymerase: Single–subunit enzyme or catalytic core of multimeric enzyme complexes?"; Proc. Natl. Acad. Sci. USA, vol. 90, pp. 5509–5513, Jun. 1993.
Thomas Pfannschmidt et al., "Separation of two classes of plastid DNA–dependent RNA polymerases that are differentially expressed in mustard (*Sinaais alba* L.) seedlings"; Plant Molecular Biology 25: 69–81, 1994.
W.R. Hess et al., "Chloroplast rps 15 and the rpoB/C1/C2 gene cluster are strongly transcribed in ribosome–deficient plastids: evidence for a functioning non–chloroplast–encoded RNA polymerase"; The EMBO Journal, vol. 12 No. 2, pp. 563–571, 1993.
Robert F. Troxler et al., "Evidence That σ factors Are Components of Chloroplast RNA Polymerase"; Plant Physiol. (1994) 104:753–759.
Rabah Iratni et al., "Regulation of rDNA transcription in chloroplasts: promoter exclusion by constitutive repression"; Genes & Development 8:2928–2938 (1994).
Lori A. Allison et al., "Light–responsive and transcription–enhancing elements regulate the plastid psbD core promoter"; The EMBO Journal, vol. 14 No. 14, pp. 101–110, (1995).
Eric Sun et al., "In Vitro Analysis of the Pea Chloroplast 16S rRNA Gene Promoter"; Molecular and Cellular Biology, Dec. 1989, vol. 9, pp. 5650–5659.
Wataru Sakamoto et al., "In vivo analysis of Chlamydomonas chloroplast petD gene expression using stable transformation of β–glucuronidase translational fusions"; Proc. Natl. Acad. Sci. USA, vol. 90, pp. 497–501, Jan. 1993.
Xing–Wang Deng et al., "Constitutive transcription and regulation of gene expression in non–photosynthetic plastids of higher plants"; The EMBO Journal, vol. 7 No. 11, pp. 3301–3308, 1988.

* cited by examiner

*Primary Examiner*—David T. Fox
*Assistant Examiner*—Anne Kubelik

(57) ABSTRACT

The present invention provides novel DNA constructs and methods for stably transforming the plastids of higher plants. The constructs described herein contain unique promoters that are transcribed by both nuclear encoded plastid polymerases and plastid encoded plastid polymerases. Use of the novel constructs of the invention facilitates transformation of a wider range of plant species and enables tissue specific expression of a transforming DNA in plastids of multicellular plants.

9 Claims, 13 Drawing Sheets

Figure 3

NUCLEAR-ENCODED TRANSCRIPTION SYSTEM IN PLASTIDS OF HIGHER PLANTS

This application is §371 of PCT/US96/12671, filed Aug. 1, 1996 which in turns claims priority under 35 U.S.C.§119 (e) to U.S. Provisional Application No. 60/002,136 filed Aug. 10, 1995.

FIELD OF THE INVENTION

The present invention relates to plant genetic engineering and particularly to plastid transformation in higher plants. The invention provides a novel promoter sequences useful for the expression of foreign genes of interest in various plant species.

BACKGROUND OF THE INVENTION

Chloroplast genes are transcribed by an RNA polymerase containing plastid-encoded subunits homologous to the $\alpha$, $\beta$ and $\beta'$ subunits of *E. coli* RNA polymerase. The promoters utilized by this enzyme are similar to *E. coil* $\sigma^{70}$-promoters, consisting of −35 and −10 consensus elements (G. L. Igloi and H. Kossel, Crit. Rev. Plant Sci. 10, 525, 1992; W. Gruissem and J. C. Tonkyn, Crit. Rev. Plant. Sci. 12:-19, 1993) Promoter selection by the plastid-encoded RNA polymerase is dependent on nuclear-encoded sigma-like factors ((Link et al. 1994, Plant promoters and transcription factors, Springer Verlag, Heidelberg, pp 63–83). In addition, transcription activity from some promoters is modulated by nuclear-encoded transcription factors interacting with elements upstream of the core promoter (L. A. Allison and P. Maliga, *EMBO J.*, 14:3721–3730; R. Iratni, L. Baeza, A. Andreeva, R. Mache, S. Lerbs-Mache, *Genes Dev.* 8, 2928, 1994). These factors mediate nuclear control of plastid gene expression in response to developmental and environmental cues.

There has been speculation of the existence of a second transcription system in plastids. However, direct evidence to support such a speculation has heretofore been unavailable. Identification of a novel second transcription system in plastids represents a significant advance in the art of plant genetic engineering. Such a system enables greater flexibility and range in plant species available for plastid transformation, and facilitates tissue specific expression of foreign proteins and RNAs via constructs that can be manipulated by recombinant DNA techniques.

SUMMARY OF THE INVENTION

This invention provides DNA constructs and methods for stably transforming plastids of multicellular plants. The DNA constructs of the invention extend the range of plant species that may be transformed and facilitate tissue specific expression of foreign genes of interest.

According to one aspect of the invention, DNA constructs are provided that contain novel promoter sequences recognized by a nuclear encoded plastid (NEP) RNA polymerase. The DNA construct contains a transforming DNA, which comprises a targeting segment, at least one cloning site adapted for insertion of at least one foreign gene of interest, the expression of the foreign gene of interest being regulated by a promoter recognized by a NEP polymerase, and a plastid selectable marker gene.

The use of promoter elements recognized by plastid encoded plastid (PEP) RNA polymerase for enhancing expression of foreign genes of interest is another aspect of the instant invention. Like the constructs described above, these constructs also contain a targeting segment, and a cloning site for expression of a foreign gene of interest.

The promoters recognized by plastid encoded plastid RNA polymerase have been well characterized in photosynthetic tissues such as leaf. In contrast, the nuclear-encoded polymerase transcription system of the present invention directs expression of plastid genes also in roots, seeds and meristematic tissue. In most plants, including maize, cotton and wheat, plant regeneration is accomplished through somatic embryogenesis (i.e., involving meristematic tissue). In a preferred embodiment of the invention, efficient plastid transformation in these crops will be greatly facilitated, through the use of the NEP plastid transcription system, promoters and polymerases of the present invention.

The NEP promoters of the invention are incorporated into currently available plastid transformation vectors and protocols for use thereof, such as those described in U.S. Pat. No. 5,451,513 and pending U.S. application Ser. No. 08/189, 256, and also described by Svab & Maliga., *Proc. Natl. Acad. Sci. USA*, 90, 913 (1993), the disclosures of which are all incorporated herein by reference. To obtain transgenic plants, plastids of non-photosynthetic tissues are transformed with selectable marker genes expressed from NEP promoters and transcribed by the nuclear-encoded polymerase. Likewise, to express proteins of interest, expression cassettes are constructed for high level expression in non-photosynthetic tissue, using the NEP promoter transcribed from the nuclear-encoded polymerase. In another aspect of the invention, PEP promoters of the invention are incorporated into currently available plastid transformation vectors and protocols for use thereof.

In yet another aspect of the invention, the NEP transcription system also may be combined with the $\sigma^{70}$-type system through the use of dual NEP/PEP promoters.

DESCRIPTION OF THE INVENTION

Figure 1:
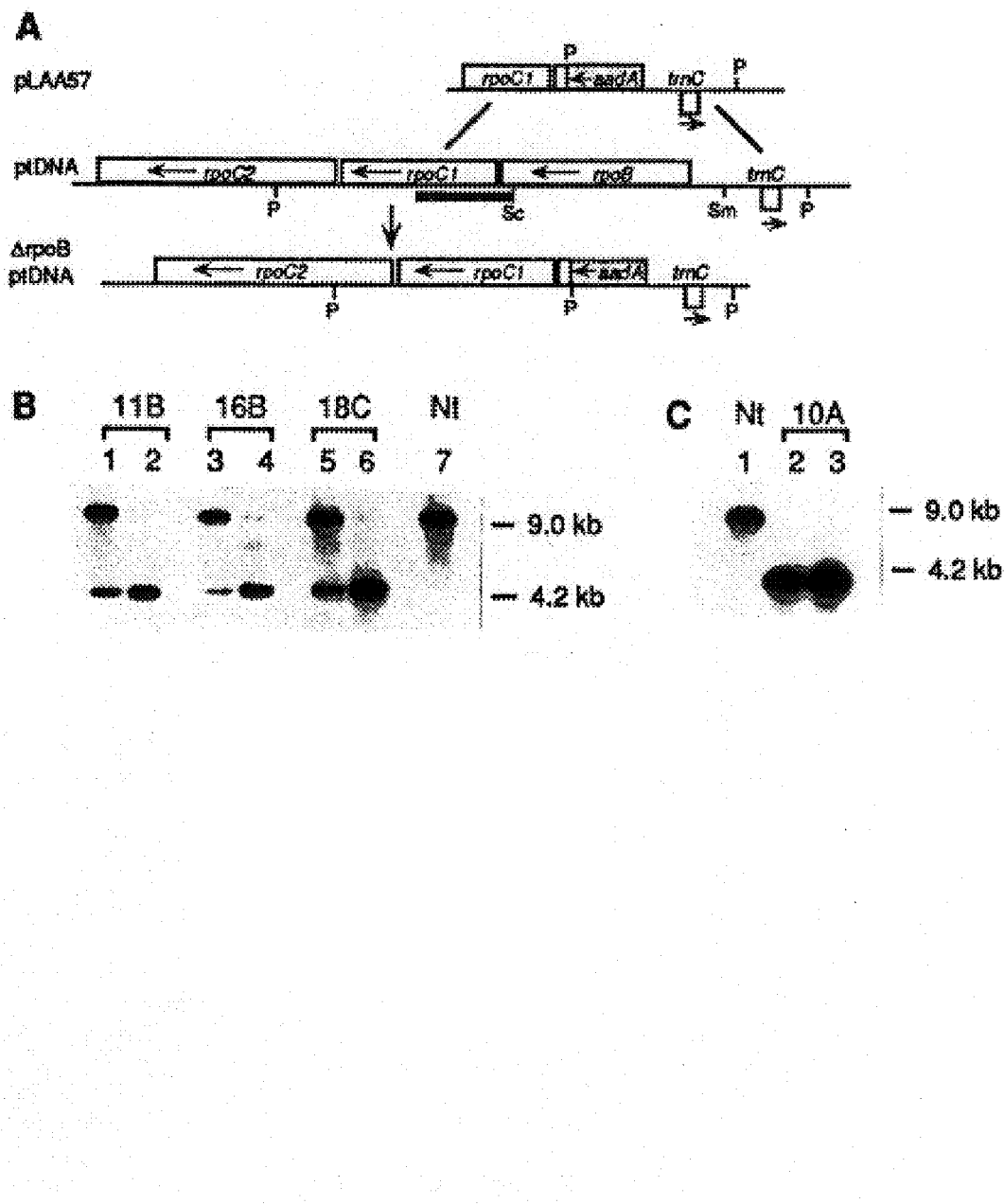
FIG. 1. Deletion of rpoB from the tobacco plastid genome by targeted gene replacement. (A) Homologous recombination (diagonal lines) via plastid DNA sequences flanking aadA in plasmid pLAA57 results in replacement of rpoB (Sac I to Sma I fragment) in the wild-type plastid genome (ptDNA) with aadA sequences, yielding the ΔrpoB plastid genome (αrpoB ptDNA). Abbreviations: rpoB, rpoC1, rpoC2 are plastid genes encoding the $\beta$, $\beta'$ and $\beta''$ subunits of the *E.coli*-like RNA polymerase; aadA is a chimeric spectinomycin-resistance gene. Restriction enzyme recognition sites: P, Pst I; Sm, Sma I; Sc, Sac I. (B) Pigment deficiency is associated with the deletion of rpoB. Total cellular DNA was isolated from green (lanes 1,3,5) and white (lanes 2,4,6) leaf tissue from three independently transformed lines (Line Nt-pLAA57-11B, lanes 1 and 2; line Nt-pLAA57-16B, lanes 3 and 4; line Nt-pLAA57-18C, lanes 5 and 6) and from wild-type green leaf tissue (Nt, lane 7). The DNA was digested with Pst I, and the gel blot was hybridized with a DNA fragment (nucleotide positions 22883–24486 of the ptDNA, numbering according to K. Shinozaki, et al., (*EMBO J.* 5, 2043, 1986)) containing part of rpoC1 (thick black line in FIG. 1A). The probe hybridizes to a 9.0 kb fragment from the wild-type genome and a 4.2 kb fragment from the ΔrpoB ptDNA. (C) DNA gel-blot analysis confirms the lack of wild-type ptDNA copies in white shoots of line Nt-pLAA57-10A (lane 2) and white seed progeny of a grafted chimeric plant from the same line (lane 3). DNA from wild-type green leaf tissue was loaded in lane 1. Note the absence of the wild-type pt DNA 9.0 kb fragment in ΔrpoB plants. The blot was prepared as for FIG. 1B.

Several reports have suggested the existence of an additional plastid-localized, nuclear-encoded RNA polymerase (reviewed in Gruissem and Tonkyn, 1993; Igloi and Kossel, 1992; Mullet, 1993; Link, 1994). By deleting the rpoB gene encoding the essential β subunit of the tobacco *E. coli*-like RNA polymerase. The existence of a second plastid transcription system which is encoded by the nucleus has been established (Allison et al., 1996, EMBO J. 15:2802–2809). Deletion of rpoB yielded photosynthetically defective, pigment-deficient plants. An examination of plastid ultrastructure in leaf mesophyll cells of the ΔrpoB plants revealed proplastid-like organelles lacking the arrays of stacked thylakoid membranes which are characteristic of photosynthetically-active chloroplasts. Transcripts for the rbcL, psbA and psbD photosynthetic genes were low, whereas mRNAs for the rpl16, atpI and 16SrDNA genes accumulated to about wild-type, or higher than in wild-type levels. Lack of transcript accumulation for the photosynthetic genes was due to lack of σ$^{70}$-type promoter activity. While in wild-type tobacco leaves the ribosomal RNA operon is normally transcribed from a σ$^{70}$-type promoter, in the ΔrpoB plants the rRNA operon was transcribed from a non-σ$^{70}$ promoter. The rRNA operon is the first transcription unit for which both a plastid-encoded and nuclear-encoded plastid RNA polymerase (PEP and NEP, respectively) was identified.

An analysis of the promoter regions of other genes has revealed that the rRNA operon is not unique. It is a member of a large class of plastid genes which have at least one promoter each for PEP and NEP, with a potential for expression by either of the two plastid RNA polymerases. In addition, plastid genes have been identified which are transcribed exclusively by NEP. Furthermore, the data suggest that additional gene-specific mechanisms regulate NEP transcript levels in different plastid types.

A NEP transcriptional start site has been identified about 62 bases upstream of the mature 16S rRNA 5' terminus. The sequence surrounding the initiation site is highly conserved among numerous plant species examined, and bears no resemblance to the PEP promoter consensus sequence. NEP promoter consensus sequences important for nuclear encoded polymerase recognition and binding (analogous to the −10 and −35 sequences of the *E. coli*-type transcription initiation site) are preferentially located within about 50 nucleotides in either direction of the NEP transcription start site. As described in greater detail in Example 1, several different NEP promoters exist, and NEP promoters are sometimes found in conjunction with PEP promoters.

The polymerases of the invention may be purified by chromatography, using standard methods. The NEP polymerase activity in column fractions can be assayed utilizing DNA segments comprising the NEP promoter region as templates in vitro transcription reactions. Alternatively, NEP promoter segments may be attached to a matrix which is separable by some means (e.g., magnetic beads). The matrix-bound DNA is incubated with a plant extract under conditions in which the nuclear encoded polymerase is expected to bind the DNA. The matrix/DNA/polymerase complex is then separated from the plant extract, and the bound protein may then be isolated and characterized. The protein purified by either of the above mentioned protocols may be used to produce antibodies to probe expression libraries, for the purpose of isolating the nuclear genes or cDNAs encoding the nuclear encoded polymerase.

As an alternative approach for the isolation of the NEP polymerase, proteins with specific affinity for the promoter fragment can be isolated and the N-terminal amino acid sequence can be determined by microsequencing. The amino acid sequence can then be used to design appropriate PCR primers for gene isolation.

The activity of the previously-known plastid-encoded σ$^{70}$-type transcription system has been well characterized in photosynthetically active tissues, such as leaf. In contrast, the nuclear-encoded polymerase transcription system of the present invention directs expression of plastid genes also in roots, seeds and meristematic tissue. In most plants, including maize, cotton and wheat, plant regeneration is accomplished through somatic embryogenesis (i.e., involving meristematic tissue). Efficient plastid transformation in these crops will be enabled, or greatly facilitated, through the use of the NEP plastid transcription system of the present invention.

The NEP promoters of the invention can be incorporated into currently available plastid transformation vectors and protocols for use thereof, such as those described in U.S. Pat. No. 5,451,513 and pending U.S. application Ser. No. 08/189, 256, and also described by Svab & Maliga., *Proc. Natl. Acad. Sci. USA*, 90, 913 (1993), all of which are incorporated herein by reference. To obtain transgenic plants, plastids of non-photosynthetic tissues are transformed with selectable marker genes expressed from NEP promoters and transcribed by the nuclear-encoded polymerase. Likewise, to express proteins of interest, expression cassettes are constructed for high level expression in non-photosynthetic tissue, using the NEP promoter transcribed from the nuclear-encoded polymerase. The NEP transcription system also may be combined with the σ$^{70}$-type system through the use of dual NEP/PEP promoters. In some cases, expression of transgenes from NEP promoters in photosynthetic tissue also may be desirable.

The detailed description set forth in Examples I–III below describes preferred methods for making and using the DNA constructs of the present invention and for practicing the methods of the invention. Any molecular cloning and recombinant DNA techniques not specifically described are carried out by standard methods, as generally set forth, for example, in Ausubel (ed.), Current Protocols in Molecular Biology. John Wiley & Sons, Inc.(1994).

The following nonlimiting Examples describe the invention in greater detail.

EXAMPLE 1

Demonstration of a Second Distinct Plastid Transcription System by Deletion of rpoB To establish the existence of a non-*E. coli*-like RNA polymerase in plastids, the gene for one of the essential subunits of the *E. coli*-like enzyme was deleted from the tobacco plastid genome. mRNA levels were then assessed in mutant plastids. The data indicate that, in the absence of the plastid-encoded *E. coli*-like enzyme, expression of some photogenes is dramatically reduced. In contrast, transcript levels for the plastid genes encoding the gene expression apparatus are similar to levels in wild-type plants. Therefore the non-*E. coli*-like RNA polymerase selectively transcribes a subset of plastid genes. This second transcription apparatus does not initiate from typical *E. coli* $\sigma^{70}$-promoters but recognizes a novel promoter sequence.

Materials and Methods for Example I

Plasmid construction. Plasmid pLAA57 is a PBSKS+ (Stratagene) derivative which carries a Sac I to Bam HI fragment (nucleotides 22658 to 29820) of the ptDNA. An internal Sac I to Sma I DNA fragment within the ptDNA insert, between nucleotides 24456 and 28192, was replaced by a chimeric spectinomycin-resistance (aadA) gene. The aadA gene is identical to that described (Z. Svab and P. Maliga, *Proc. Natl. Acad. Sci. USA*, 90, 913, 1993), except that the psbA 3' region is shorter and is contained in an Xba I to Dra I fragment as described (J. M. Staub and P. Maliga, *Plant J*. 6, 547, 1994).

Plant Transformation. For plastid transformation tungsten particles were coated (Z. Svab and P. Maliga, *Proc. Natl. Acad. Sci. USA*, 90, 913, 1993) with pLAA57 DNA, and introduced into the leaves of *Nicotiana tabacum* plants using the DuPont PDS1000He Biolistic gun at 1100 p.s.i. Transgenic shoots were selected aseptically on RMOP medium (Z. Svab, P. Hajdukiewicz, P. Maliga, *Proc. Natl. Acad. Sci. USA* 87, 8526, 1990) containing 500 mg/ml spectinomycin dihydrochloride. Transgenic cuttings were rooted and maintained on RM medium consisting of agar-solidified MS salts (T. Murashige and F. Skoog, *Physiol. Plant*., 15, 493, 1962) containing 3% sucrose.

Electron Hicroscopy. Electron microscopy was done on fully expanded leaves from wild-type and ΔrpoB cuttings grown in sterile culture on RM medium with 3% sucrose. Tissue was fixed for 2 hours in 2% glutaraldehyde, 0.2M sucrose, 0.1M phosphate buffer (pH 6.8) at room temperature, and washed three times in 0.2M sucrose, 0.1M phosphate buffer. Fixed tissues were postfixed in buffered 1% osmium tetroxide with 0.2M sucrose, dehydrated in a graded ethanol series, embedded in Spurr's epoxy resin (hard), sectioned, and stained with uranyl acetate and lead citrate for transmission electron microscopy.

Gel blots. Total leaf DNA was prepared as described (I. J. Mettler, *Plant Mol. Biol. Rep*., 5, 346, 1987), digested with restriction endonuclease Pst I, separated on 0.7% agarose gels, and transferred to Hybond N (Amersham) using the Posiblot Transfer apparatus (Stratagene). Hybridization to a random-prime labeled fragment was carried out in Rapid Hybridization Buffer (Amersham) overnight at 65° C. Total leaf RNA was prepared using TRIzol (GIBCO BRL), following the manufacturer's protocol. The RNA was electrophoresed on 1% agarose/formaldehyde gels, then transferred to nylon membrane and probed as for the DNA blots.

Synthesis of Probes. Double-stranded DNA probes for psbA, atpI, and rpl16 were prepared by random-primed $^{32}$P-labeling of PCR-generated DNA fragments. The sequence of the primers used for PCR, along with their positions within the tobacco ptDNA (K. Shinozaki, et al., *EMBO J*. 5, 2043, 1986) are as follows: psbA, 5' primer= 5'-CGCTTCTGTAACTGG-3' (SEQ ID NO: 1) (complementary to nucleotides 1550 to 1536 of the ptDNA), 3' primer=5'-TGACTGTCAACTACAG-3' (SEQ ID NO: 2) (nucleotides 667 to 682); atpI 5' primer=5'-GTTCCATCAATACTC-3' (SEQ ID NO: 3) (complementary to nucleotides 15985 to 15971), 3' primer= 5'-GCCGCGGCTAAAGTT-3' (SEQ ID NO: 4) (nucleotides 15292 to 15306); rpl16 5' primer=5'-TCCCACGTTCAAGGT-3' (SEQ ID NO: 5) (complementary to nucleotides 84244 to 84230), 3' primer= 5'-TGAGTTCGTATAGGC-3' (SEQ ID NO: 6) (nucleotides 83685 to 83699). To generate probes for rbcL, psbD/C and 16S rRNA, the following restricted DNA fragments were $^{32}$P-labeled: rbcL, a Bam HI fragment (nucleotides 58047 to 59285 in the ptDNA); psbD/C, a Sac II to Hind III fragment of the tobacco psbD/C operon (nucleotides 34691–36393); 16S rRNA, an Eco RI to Eco RV fragment (nucleotides 138447 to 140855 in the ptDNA).

Figure 3A:
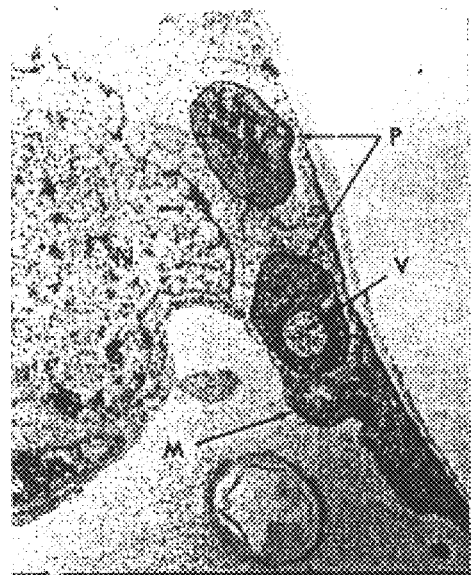
FIG. 3. (A) Plastids (P) in leaf mesophyll cells of ΔrpoB plants lack organized photosynthetic membranes. Abbreviations: N, nucleus; V, vesicles, M, mitochondrion (B) For comparison an electron micrograph of a wild-type leaf chloroplast (Cp) with thylakoid membranes (T) is shown. Magnification in both (A) and (B) is 7,800×.
Figure 3B:
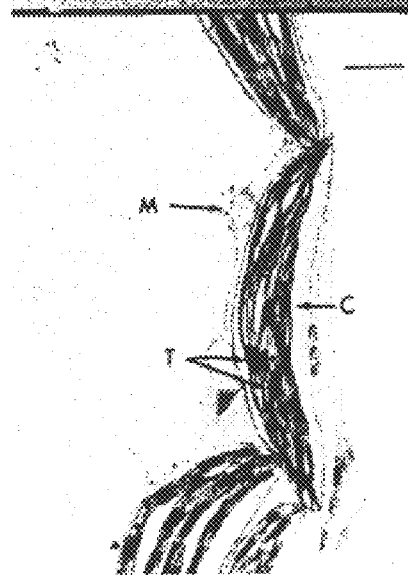

Normalizing DNA levels by plastid genome copy number. To test whether changes in plastid genome copy number contributed to the estimated differences in gene expression, total cellular DNA and RNA were prepared from equal amounts of leaf tissue from wild-type and ΔrpoB plants. To compare the number of plastid genome copies per equivalent leaf mass, DNA gel-blots were carried out with an equal volume of each DNA preparation and probed with a radiolabeled Eco RI to Eco RV fragment (from nucleotides 138447 to 140845 of ptDNA (K. Shinozaki, et al., *EMBO J*. 5, 2043, 1986) of 16SrDNA sequence. Quantitation by PhosphorImage analysis demonstrated an equal number of plastid genome copies in each sample. The amount of 16S rRNA from equal tissue samples, as measured by RNA gel-blots on equal volumes of each RNA preparation, was reduced by 2.5-fold in the ΔrpoB plants. This value is similar to the 3-fold reduction estimated when normalizing with the cytoplasmic 25S rRNA signal (FIG. 3B).

Primer extension reactions. Primer extension reactions were carried out on 3 μg (wild-type) or 10 μg (ΔrpoB) of total leaf RNA as described (L. A. Allison and P. Maliga, *EMBO J*., in press) using the following primers: 16S rRNA: 5'-TTCATAGTTGCATTACTTATAGCTTC-3' (SEQ ID NO: 7)(complementary to nucleotides 102757–102732); rbcL: 5'-ACTTGCTTTAGTCTCTGTTTGTGGTGACAT (SEQ ID NO: 8)(complementary to nucleotides 57616–57587). Sequence ladders were generated with the same primers using the Sequenase II kit (USB).

Identification of primary transcripts by in vitro capping. Total leaf RNA (20 μg) from wild-type and ΔrpoB plants was capped in the presence of [α-$^{32}$P]GTP (J. C. Kennell and D. R. Pring, *Mol. Gen. Genet*. 216, 16, 1989). Labeled 16S rRNAs were detected by ribonuclease protection (A. Vera and M. Sugiura, *Plant Mol. Biol*. 19, 309, 1992) using the RPAII kit (Ambion). To prepare the protecting complementary RNA, the 16SrDNA upstream region (nucleotides 102526–102761 of the ptDNA) was PCR-amplified using the following primers: 5'primer was 5'-CCTCTAGACCCTAAGCCCAATGTG-3' (SEQ ID NO: 9) corresponding to nucleotides 102526 and 102541 of the ptDNA (K. Shinozaki, et al. , EMBO J. 5, 2043, 1986), underlined) plus an XbaI site; 3' primer was 5'-CCGGTACCGAGATTCATAGTTGCATTAC-3' (SEQ ID NO: 10) complementary to nucleotides 102761 to 102742 of the ptDNA (underlined) plus a Kpn I site. The amplified product was cloned as an Xba I to Kpn I fragment into Xba I and Kpn I-restricted pBSKS+ vector (Stratagene). To generate unlabeled RNA complimentary to the 5' end of 16S rRNAs, the resulting plasmid was linearized with Xba I, and transcribed in a Megascript (Ambion) reaction with T3 RNA polymerase. Markers (100, 200, 300, 400, and 500 nucleotides) were prepared with the RNA Century Markers Template Set (Ambion), following the manufacturer's protocol. The 72 nucleotide marker was the mature processed transcript from the plastid trnV gene, and was generated by RNAse protection.

Results and Discussion

Disruption of the *E. coli*-like RNA polymerase activity in tobacco plastids results in a pigment-deficient phenotype. To avoid disrupting plastid genes for other functions the rpoB gene was targeted for deletion, since it is the first reading frame of an operon encoding exclusively subunits of the *E. coli*-like plastid polymerase (K. Shinozaki, et al. , *EMBO J.* 5, 2043, 1986). The deletion was accomplished by replacing most of the rpoB coding region (3015 out of 3212 base pairs) and 691 bp of upstream non-coding sequence, with a chimeric spectinomycin resistance (aadA) gene (Z. Svab and P. Maliga, *Proc. Natl. Acad. Sci. USA*, 90, 913, 1993) in a cloned plastid DNA (ptDNA) fragment. The resulting plasmid was introduced by particle bombardment into tobacco chloroplasts, where the aadA gene integrated into the plastid genome via flanking plastid DNA sequences as diagrammed in FIG. 1A. Since the plastid genetic system is highly polyploid, with every leaf cell containing up to 10,000 identical copies of the ptDNA, selective amplification of transformed genome copies was carried out by growing the bombarded tissue on spectinomycin-containing medium (P. Maliga, *Trends Biotechnol.* 11, 101, 1993).

Figure 2:
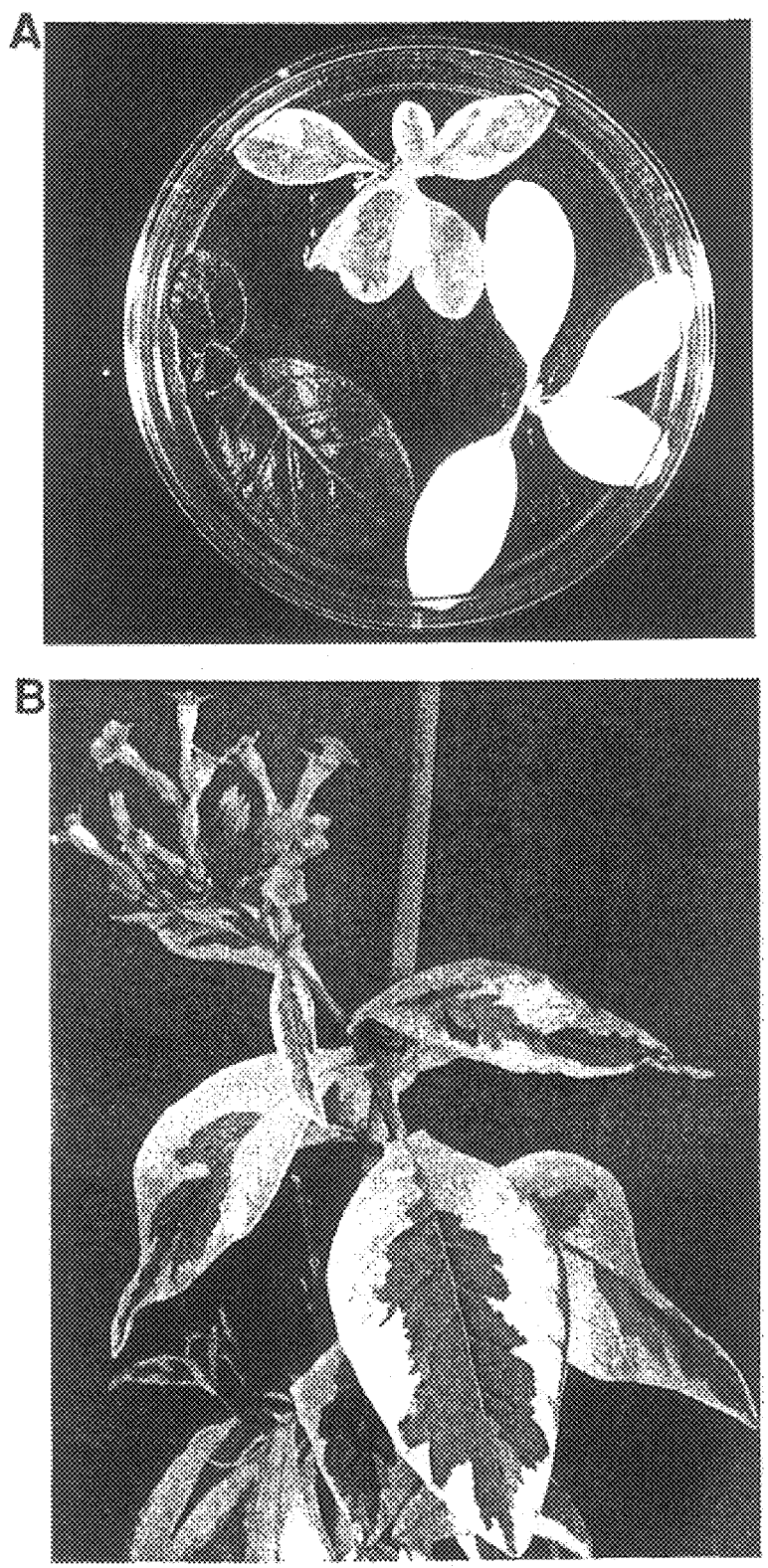
FIG. 2. Deletion of rpoB results in a pigment-deficient phenotype. (A) Green wild-type (left), pigment-deficient ΔrpoB (right), and chimeric (center) plants are shown. (B) A flowering chimeric plant in the greenhouse. Note the white leaf margins indicating ΔrpoB plastids in the second leaf layer which forms the germline cells.

From the initial round of selection several spectinomycin-resistant plants exhibiting sectors of white leaf tissue were obtained (FIG. 2A). DNA gel-blot analysis of white and green sectors indicated that the pigment-deficiency was correlated with deletion of rpoB in three independently transformed lines (FIG. 1B). Most DNA samples from the pigment-deficient tissue, for example lane 4 in FIG. 1B, contained a mix of wild-type and transformed genome copies. The complete absence of wild-type ptDNA copies was critical for the interpretation of the data. Therefore, to obtain plants containing only transformed plastid genomes, shoots were regenerated from the white tissue sectors. This procedure yielded uniformly white plants (FIG. 2A) which contained no wild-type ptDNA as judged by DNA gel-blot analysis (FIG. 1C). Regeneration from these white leaves on spectinomycin-free medium yielded exclusively pigment-deficient shoots, confirming the complete absence of wild-type plastid genomes in all leaf layers and cell types.

It is difficult to obtain seed from tobacco plants grown in sterile culture. Fortuitously, during plant regeneration from primary transformants, we obtained a periclinal chimera (S. Poethig, *Trends Genetics* 5, 273, 1989) homoplasmic for the plastid mutation in the L2 leaf layer (FIG. 2A). This line was grafted on wild-type tobacco and was raised to maturity in the greenhouse (FIG. 2B). Seed from self-pollinated flowers gave rise to uniformly white seedlings, in which no wild-type plastid genomes could be detected by DNA gel-blot analysis (FIG. 1C).

Plastids in leaves of the ΔrpoB plants lack thylakoid membranes. The pigment-deficient ΔrpoB plants were unable to grow photoautotrophically. However, if maintained on sucrose-containing medium to compensate for their lack of photosynthesis, they grew normally but at a reduced rate compared to wild-type plants, and exhibited no noticeable changes in organ morphology. Moreover, ΔrpoB seedlings germinated at a high efficiency, and developed into plants. These observations indicate that the *E. coli*-like plastid RNA polymerase is not required for maintenance of the nonphotosynthetic plastid functions necessary for plant growth and differentiation.

An examination of plastid ultrastructure in leaf mesophyll cells of the ΔrpoB plants revealed that the mutant plastids were smaller and rounder than wild-type chloroplasts, averaging 2–5 μm in length as compared to 5–9 μm for wild-type chloroplasts. The ΔrpoB plastids are thus larger than undifferentiated proplastids whose average size is 1 μm (M. R. Thomas and R. J. Rose, *Planta* 158, 329, 1983). In addition, ΔrpoB plastids typically contained multiple vesicles of irregular size and shape, and lacked the arrays of stacked thylakoid membranes which are characteristic of photosynthetically-active chloroplasts (FIG. 3).

Transcription of plastid genes is maintained in ΔrpoB plastids. In the absence of the β subunit, no transcription was expected from plastid $\sigma^{70}$-type promoters. To determine whether any transcription activity was maintained in the ΔrpoB plastids, accumulation of RNAs was examined by RNA gel-blot analysis. Transcripts were surveyed for two different classes of plastid genes (K. Shinozaki, et al.,*EMBO J.* 5, 2043, 1986). The first group included genes encoding subunits of the photosynthetic apparatus: the psbD/C operon, encoding subunits D2 and CP43 of photosystem II; rbcL, encoding the large subunit of ribulose-1,5-bisphosphate carboxylase; and psbA, encoding the D1 subunit of the photosystem II reaction center. The second group contained genes for components of the gene expression apparatus: rpl16 encoding a ribosomal protein subunit, and the 16SrDNA gene. All plastid RNA quantitations were normalized to cytoplasmic 25S ribosomal RNA levels.

Figure 4:
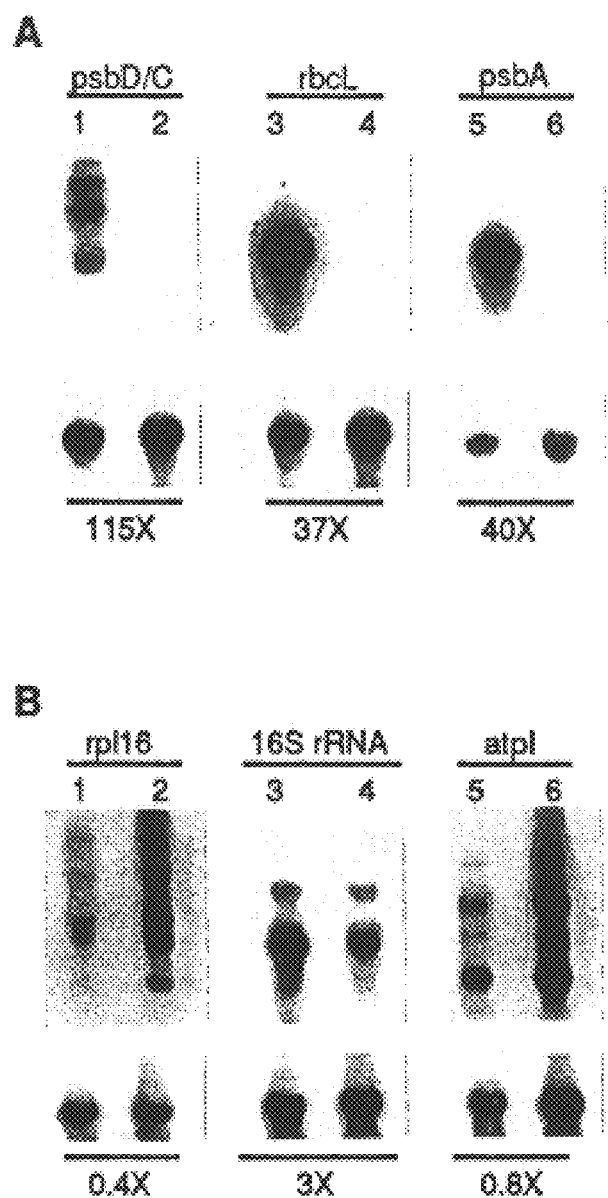
FIG. 4. (Upper) Accumulation of plastid mRNAs for (A) photosynthetic genes and (B) genetic system genes in the ΔrpoB plants. Gel blots were prepared with total cellular RNA (A, 3 μg per lane; B, 5 μg per lane) from wild-type (lanes 1,3,5) and ΔrpoB (lanes 2,4,6) leaf tissue, and hybridized to the indicated plastid gene sequences. (Lower) Blots shown above were reprobed with 25S rDNA sequences. Hybridization signals were quantified with a Molecular Dynamics PhosphorImager and normalized to the 25S rRNA signal. The fold excess of wild-type over ΔrpoB signal intensities for each probe is shown below the lanes.

Surprisingly, accumulation of mRNAs was detected for all the genes examined. However, the effect of the rpoB deletion on transcript accumulation was dramatically different for the two classes of genes. The steady-state mRNA levels of the photosynthetic genes psbD/C, rbcL, and psbA, were reduced 40- to 100-fold compared to wild-type levels (FIG. 4A; signals were visible in all ΔrpoB lanes upon longer exposure). In contrast, transcript levels for nuclear encoded polymerase genes were much less affected. A 3-fold reduction for 16S rRNA was measured, and an actual increase for the multiple transcripts arising from the polycistronic operon containing the rpl16 gene was also observed (FIG. 4B). These data indicate that, while expression of genes encoding the photosynthetic apparatus is defective in the ΔrpoB plants, the RNAs for genes involved in housekeeping functions accumulate to approximately wild-type, or higher, levels.

The 16SrDNA gene is transcribed from a novel promoter in ΔrpoB plants. The accumulation of plastid RNAs confirmed that there is RNA polymerase activity in plastids lacking the β subunit of the *E. coli*-like enzyme. However, migration of plastid genes to the nucleus has been documented (S. L. Baldauf and J. D. Palmer, *Nature* 334, 262, 1990; J. S. Gantt, S. L. Baldauf, P. J. Calie, N. F. Weeden, J. D. Palmer, *EMBO J*. 10, 3073, 1991; M. W. Gray, *Curr. Op. Genet. Dev.* 3, 884, 1993). Therefore, transcription in ΔrpoB plastids could still conceivably initiate from $\sigma^{70}$-type promoters if there existed a nuclear copy of rpoB, whose product could be imported into plastids and assembled into functional *E. coli*-like enzyme. To establish whether the plastid transcripts detected in ΔrpoB plants were products of transcription from a $\sigma^{70}$-type promoter, the 5' transcript ends for four genes were mapped, rbcL (K. Shinozaki and M. Sugiura, *Gene* 20, 91, 1982), 16SrDNA (A. Vera and M. Sugiura, *Curr. Genet.* 27, 280, 1995), psbA (M. Sugita and M. Sugiura, *Mol. Gen. Genet.* 195, 308, 1984) and psbD (W. B. Yao, B. Y. Meng, M. Tanaka, M. Sugiura, *Nucl. Acids Res.* 17, 9583, 1989), for which the transcription initiation sites have been established previously. None of the 5' ends mapped to $\sigma^{70}$-type promoter initiation sites (data are shown for rbcL and 16SrDNA in FIG. 5A). Therefore it was concluded that the residual RNA polymerase activity in the ΔrpoB plastids was not due to an *E. coli*-like enzyme, but represents a second unique plastid transcription system. This distinct RNA polymerase enzyme is referred to as the Nuclear Encoded Plastid RNA polymerase (NEP), to distinguish it from the *E. coli*-like enzyme which we designate Plastid Encoded Plastid RNA polymerase (PEP). Since the tobacco plastid genome has been fully sequenced, and since the few unidentified reading frames bear no sequence similarity to known RNA polymerase subunits (K. Shinozaki, et al. *EMBO J*. 5, 2043, 1986), transcription by the nuclear encoded RNA polymerase relies on nuclear gene products.

In the absence of transcription from $\sigma^{70}$-type promoters in the ΔrpoB plants, the question remained: what promoters were the source of the plastid RNAs. The 16S rRNA 5' end detected in the ΔrpoB plants mapped 62 nucleotides upstream of the mature 16S rRNA 5' terminus (FIG. 5A). This 5' end was determined to be a primary transcript by in vitro capping (FIG. 5B). A prominent primary transcript with a similar 5' end was recently reported in proplastids of heterotrophically-cultured tobacco cells, and was designated P2 (A. Vera and M. Sugiura, *Curr. Genet.* 27, 280, 1995; This transcript is also present at very low levels in wild-type leaf cells (A. Vera and M. Sugiura, *Curr. Genet.* 27, 280, 1995; FIG. 5A longer exposure, not shown). The sequence surrounding the initiation site is highly conserved among all plant species examined, and bears no resemblance to the $\sigma^{70}$ consensus sequence (A. Vera and M. Sugiura, *Curr. Genet.* 27, 280, 1995). Based on its prominent usage in the ΔrpoB plants, it was concluded that this unique promoter is utilized by the NEP transcription apparatus.

Figure 5:
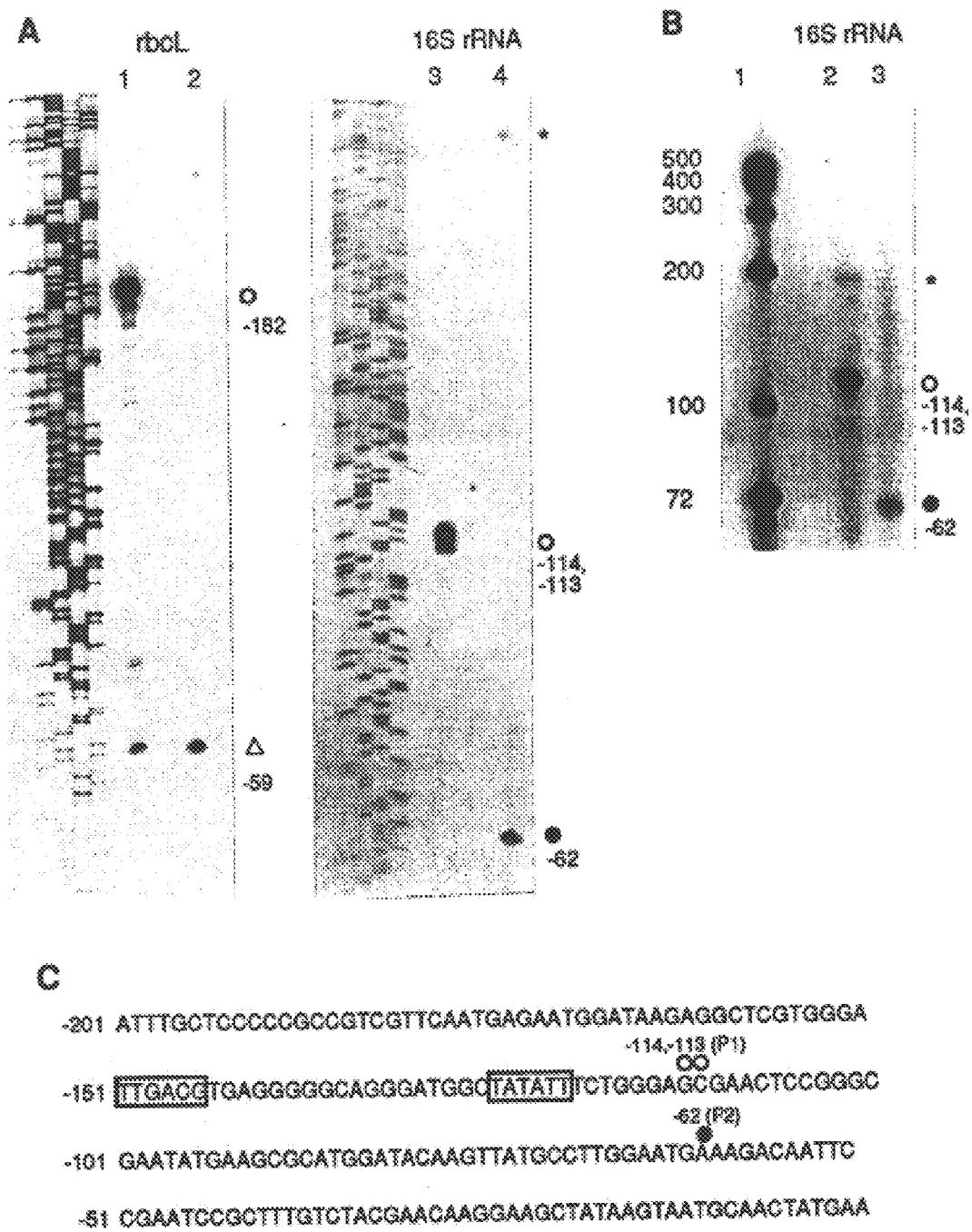
FIG. 5. Transcription in the ΔrpoB plants initiates from a non-canonical promoter. (A) Primer extension analysis was used to map the 5' ends of rbcL and 16SrDNA transcripts in wild-type (lanes 1,3) and ΔrpoB (lanes 2,4) plants. Primary transcripts are marked by circles (open for wild-type, closed for ΔrpoB), processed transcripts by a triangle. Transcriots of unknown origin are starred. The accompanying sequence ladders (loading order GATC) were generated using the same primers that served in the primer extension reactions. Numbers beside each extension product mark the distance from the first nucleotide of the coding sequence for rbcL and from the first nucleotide of the mature 16S rRNA. (B) Mapping primary transcripts for 16S rRNA in wild-type (lane 2) and ΔrpoB (lane 3) plants. Total leaf RNA (20 μg) was capped in vitro, and capped 16S rRNA species were identified by RNAse protection after hybridization with a complementary RNA probe. Capped protected products are marked as in (A). Lane 1 contains RNA standards of the sizes indicated. (C) DNA sequence of the 16SrDNA upstream region with transcripts initiating from promoters for the plastid-encoded ($\sigma^{70}$-type, P1) and nuclear-encoded (P2) polymerases (designation of P1 and P2 is based on A. Vera and M. Sugiura, *Curr. Genet.* 27, 280, 1995; SEQ ID NO: 58). Consensus $\sigma^{70}$ promoter elements (−35 and −10) are boxed. Initiation sites are marked by circles, as in (A) and (B). Numbering begins from the first nucleotide upstream of the 16SrDNA coding region (−1=nucleotide 102757 in the tobacco plastid genome).

In contrast to the 16S rRNA, the major transcripts for the photosynthetic genes rbcL, and psbD/C mapped to previously-characterized processed ends (data shown for rbcL FIG. 5; L. Hanley-Bowdoin, E. M. Orozco, N.-H. Chua, *Mol. Cell. Biol.* 5, 2733, 1985; J. E. Mullet, E. M. Orozco, N.-H. Chua, *Plant Mol. Biol.* 4, 39, 1985; S. Reinbothe, C. Reinbothe, C. Heintzen, C. Seidenbecher, B. Parthier, *EMBO J*. 12, 1505, 1993). Additional minor transcript ends mapped upstream of the processed termini. Therefore, the low levels of transcript accumulation for these photosynthetic genes are the result of upstream promoter activity and subsequent processing of the readthrough RNAs to yield correctly-sized transcripts.

Proposed roles for the two plastid transcription systems. In the ΔrpoB plants there is accumulation of RNAs transcribed by the NEP system. This indicates a role for the nuclear encoded RNA polymerase in maintaining the expression of plastid housekeeping genes. Apparently these expression levels are sufficient to support the growth and differentiation of non-photoautotrophic plants. In contrast, the *E. coli*-like PEP RNA polymerase is required to provide the high levels of plastid gene transcripts necessary for development of photosynthetically active chloroplasts. The proposed role for the nuclear encoded RNA polymerase implies a high demand for its function during the early phases of chloroplast development, before the PEP RNA polymerase is active (J. E. Mullet, *Plant Physiol.*, 103, 309, 1993). Developmental regulation of a nuclear-encoded RNA polymerase is supported by the observation that the nuclear encoded polymerase P2 promoter of the 16SrDNA gene is more active in proplastids of cultured tobacco cells than in leaf chloroplasts (A. Vera and M. Sugiura, *Curr. Genet.* 27, 280, 1995).

EXAMPLE II

Transcription by Two Distinct RNA Polymerases is a General Regulatory Mechanism of Gene Expression in Higher Plants As described in Example I, accumulation of transcripts in plants lacking the PEP polymerase led to the identification of a NEP promoter for the plastid ribosomal RNA operon (Allison et al. 1996, EMBO J. 14:3721–3730). To facilitate mapping of additional NEP promoters, mRNA accumulation was examined in ΔrpoB plants for most classes of plastid genes. The novel promoter sequences described herein may be used to extend the range of species within such plastid transformation is feasible and to drive expression of foreign genes of interest in a tissue specific manner.

Materials and Methods for Example II

RNA Gel blots Total leaf RNA was prepared using TRIzol (GIBCO BRL), following the manufacturer's protocol. The RNA was electrophoresed on 1% agarose/formaldehyde gels, then transferred to Hybond N (Amersham) using the Posiblot Transfer apparatus (Stratagene). Hybridization to random-primer labeled fragment was carried out in Rapid Hybridization Buffer (Amersham) overnight at 65° C. Double-stranded DNA probes were prepared by random-primed $^{32}$P-labeling of PCR-generated DNA fragments. The sequence of the primers used for PCR, along with their positions within the tobacco ptDNA (Shinozaki, et al. 1986, supra) are as follows:

| Gene | 5' nucleotide position in plastid DNA | Sequence |
|---|---|---|
| accD | 60221 | GGATTTAGGGGCGAA SEQ ID NO: 11 |
|  | 60875 | GTGATTTTCTCTCCG SEQ ID NO: 12 |
| atpB | 56370(C) | AGATCTGCGCCCGCC SEQ ID NO: 13 |
|  | 55623 | CCTCACCAACGATCC SEQ ID NO: 14 |
| atpI | 15985(C) | GTTCCATCAATACTC SEQ ID NO: 3 |
|  | 15292 | GCCGCGGCTAAAGTT SEQ ID NO: 4 |
| clpP | 73621(C) | GACTTTATCGAGAAAG SEQ ID NO: 15 |
|  | 73340 | GAGGGAATGCTAGACG SEQ ID NO: 16 |

| Gene | 5' nucleotide position in plastid DNA | Sequence |
|---|---|---|
| ndhA | 122115(C) | GATATAGTGGAAGCG SEQ ID NO: 17 |
| | 121602 | GTGAAAGAAGTTGGG SEQ ID NO: 18 |
| ndhB | 97792(C) | CAGTCGTTGCTTTTC SEQ ID NO: 19 |
| | 97057 | CTATCCTGAGCAATT SEQ ID NO: 20 |
| ndhF | 113366(C) | CTCGGCTTCTTCCTC SEQ ID NO: 21 |
| | 112749 | CTCCGTTTTTACCCC SEQ ID NO: 22 |
| ORF1901 | 129496(C) | GTGACTATCAAGAGG SEQ ID NO: 23 |
| | 128895 | GACTAACATACGCCCG SEQ ID NO: 24 |
| ORF2280 | 92881 | GCTCGGGAGTTCCTC SEQ ID NO: 25 |
| | 93552 | TGCTCCCGGTTGTTC SEQ ID NO: 26 |
| petB | 78221 | GGTTCGAAGAACGTC SEQ ID NO: 27 |
| | 78842 | GGCCCAGAAATACCT SEQ ID NO: 28 |
| psaA | 43467(C) | TTCGTTCGCCGGAACC SEQ ID NO: 29 |
| | 42743 | GATCTCGATTCAAGAT SEQ ID NO: 30 |
| psbB | 75241 | GGAGCACATATTGTG SEQ ID NO: 31 |
| | 75905 | GGATTATTGCCGATG SEQ ID NO: 32 |
| psbE | 66772 (C) | CAATATCAGCAATGCAGTTCATCC SEQ ID NO: 33 |
| | 66452 | GGAATCCTTCCAGTAGTATCGGCC SEQ ID NO: 34 |
| rps14 | 38621 | CACGAAGTATGTGTCCGGATAGTCC SEQ ID NO: 35 |
| rpl33/rpl18 | 70133 | GGAAAGATGTCCGAG SEQ ID NO: 36 |
| | 70636 | GTTCACTAATAAATCGAC SEQ ID NO: 37 |

The rps16 mRNA was probed with an EcoRI fragment isolated from plasmid pJS40, containing sequences between nucleotides 4938/5363 and 6149/6656 of the tobacco ptDNA (Shinozaki et al., 1986, supra). The probe for tobacco 25S rRNA was from plasmid pKDR1 (Dempsey et al., Mol. Plant Path. 83:1021, 1993) containing a 3.75 kb EcoRI fragment from a tobacco 25S/18S locus cloned in plasmid pBR325. When hybridizing gel-blots for 25S rRNA, $^{32}$P-labeled double-stranded DNA probe was mixed with unlabeled plasmid pKDR1 corresponding to a 2-fold excess over the amount of RNA present on the filter.

Primer extension reactions Primer extension reactions were carried out on 10 μg (wild-type) or 10 μg (ΔrpoB) of total leaf RNA as described (Allison and Maliga, 1995 EMBO J. 15:2802–2809). The primers are listed below. Underlined oligonucleotides were also used to generate the capping constructs.

| Gene | 5' nucleotide position in plastid DNA | Sequence |
|---|---|---|
| accD | 59758 | CCGAGCTCTTATTTCCTATCAGACTAAGC SEQ ID NO: 38 |

| Gene | 5' nucleotide position in plastid DNA | Sequence |
|---|---|---|
| atpB | 56736 | CCCCAGAACCAGAAGTAGTAGGATTGA SEQ ID NO: 39 |
| atpI | 15973 | GTATTGATGGAACATGATAGAACAT SEQ ID NO: 40 |
| clpP#1 | 74479 | GGGACTTTTGGAACACCAATAGGCAT SEQ ID NO: 41 |
| clpP#2 | 74947 | GGGAGCTCCATGGGTTTGCCTTGG SEQ ID NO: 42 |
| ORF1901 | 31451 | CTTCATGCATAAGGATACTAGATTACC SEQ ID NO: 43 |
| ORF2280 | 87419 | GGGAGCTCTACATGAAGAACATAAGCC SEQ ID NO: 44 |
| rps2 | 16921 | CCAATATCTTCTTGTCATTTCTCTC SEQ ID NO: 45 |
| rps16 | 6185 | CATCGTTTCAAACGAAGTTTTACCAT SEQ ID NO: 46 |

Sequence ladders were generated with the same primers using the Sequenase II kit (USB).

Identification of primary transcripts by in vitro capping Total leaf RNA (20 mg) from wild-type and ΔrpoB plants was capped in the presence of [a-32P]GTP (Kennell and Pring, 1989 Mol Gen. Genet., 216:16–24). Labeled RNAs were detected by ribonuclease protection (Vera and Sugiura, 1992, supra) using the RPAII kit (Ambion). To prepare the protecting complementary RNA, the 16SrDNA upstream region (nucleotides 102526–102761 of the ptDNA) was PCR-amplified using the primers listed below. The 5' primers were designed to add an XbaI restriction site(underlined) upstream of the amplified fragment. The 3' primers were designed to add a KpnI site (underlined) downstream of the amplified sequence. The amplified product was cloned as an XbaI to KpnI fragment into XbaI- and KpnI-restricted PBSKS+ vector (Stratagene). To generate unlabeled RNA complementary to the 5' end of RNAs, the resulting plasmid was linearized with XbaI, and transcribed in a Megascript (Ambion) reaction with T3 RNA polymerase. Markers (100, 200, 300, 400, and 500 nucleotides) were prepared with the RNA Century Markers Template Set (Ambion), following the manufacturer's protocol.

| Gene | 5' nucleotide position in plastid DNA | Sequence |
|---|---|---|
| accD | 59758 | CCGAGCTCTTATTTCCTATCAGACTAAGC SEQ ID NO: 38 |
| | 59576 | CCGGTACCATAGGAGAAGCCGCCC SEQ ID NO: 47 |
| atpB | 56750 | CCGAGCTCGTAGTAGGATTGATTCTCA SEQ ID NO: 48 |
| | 57131(C) | CCGGTACCGGAGCCAATTAGATACAAA SEQ ID NO: 49 |
| atpI | 15895 | CCGAGCTCTGACTTGGAAACCCCC SEQ ID NO: 50 |
| | 16277(C) | CCGAATTCTAGTATTCGCAATTTGT SEQ ID NO: 51 |
| clpP | 74462 | GGGAGCTCCAGGACTTCGGAAAGG SEQ ID NO: 52 |
| | 74752(C) | GGGGTACCAATACGCAATGGGG SEQ ID NO: 53 |
| | 74947 | GGGAGCTCCATGGGTTTGCCTTGG SEQ ID NO: 42 |
| | 75080(C) | GGGGTACCGCTAATTCATACAGAG SEQ ID NO: 54 |

-continued

| Gene | 5' nucleotide position in plastid DNA | Sequence |
|---|---|---|
| ORF1901 | 31424 | GGGAGCTCCGACCACAACGACCG SEQ ID NO: 55 |
|  | 31724(C) | GGGGTACCCTTACATGCCTCATTTC SEQ ID NO: 56 |
| ORF2280 | 87419 | GGGAGCTCTACATGAAGAACATAAGCC SEQ ID NO: 44 |
|  | 87154 | GGGGTACCGTGCCTAAGGGCATATCGG SEQ ID NO: 57 |

DNA sequence analysis DNA sequence analysis was carried out utilizing the Wisconsin Sequence Analysis Package (Genetics Computer Group, Inc.).

Results and Discussion

Figure 6:
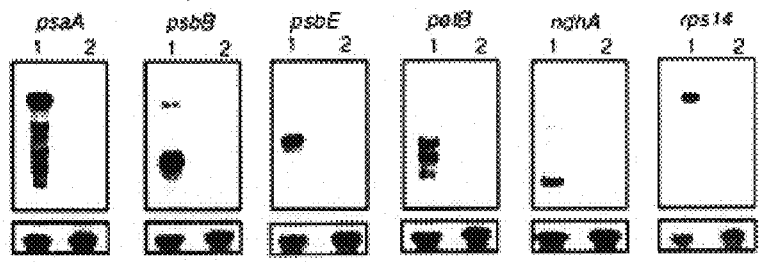
FIG. 6. Accumulation of plastid mRNAs in wild-type and ΔrpoB tobacco leaves. Blots for the plastid genes (see Example I) are grouped as follows. (A) mRNA is significantly more abundant in the leaves of wild-type than in ΔrpoB plants. (B) Levels of mRNA are comparable in wild-type and ΔrpoB leaves, or (C) are higher in ΔrpoB leaves. Gel blots were prepared with total cellular RNA (3 μg per lane) from wild-type (lanes 1) and ΔrpoB (lanes 2) leaf tissue, and hybridized to the indicated plastid gene sequences. (Lower panel) To control for loading, blots shown above were reprobed with 25S rDNA sequences.
Figure 6:
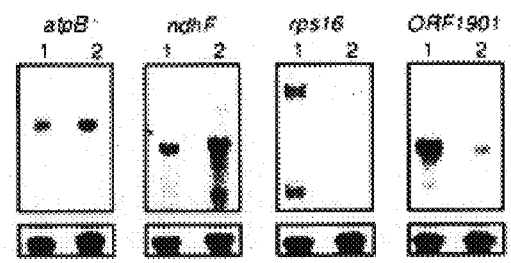
Figure 6:
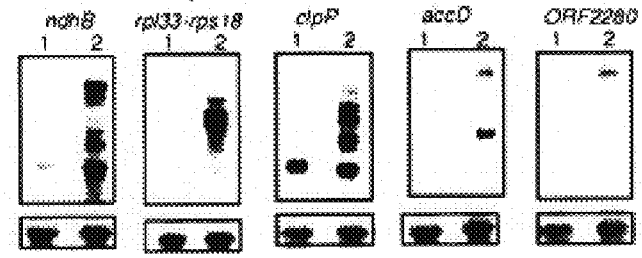

Based on the accumulation of mRNAs in wild-type and ΔrpoB leaves, the plastid genes may be divided into three classes. The first class includes genes for which the mRNAs accumulate to high levels in wild-type leaves, and to very low levels in the leaves of ΔrpoB plants (FIG. 6A). Genes which belong to this class are psaA (photosystem I gene), psbB and psbE (photosystem II genes), petB (cytochrome b6/f complex gene), ndhA (respiratory chain NADH dehydrogenase homologue; Matsubayashi et al., 1987 Mol. Gen. Genet. 210:385:393) and rps14 (ribosomal protein gene). The second class includes plastid genes for which the mRNAs accumulate to about equal levels in the wild-type and (rpoB leaves (FIG. 6B). This class includes atpB (ATP synthase gene), ndhF (respiratory chain NADH dehydrogenase homologue gene; Matsubayashi et al., 1987, supra), rps16 (ribosomal protein gene) and ORF1901 (a gene with unknown function; Wolfe et al., 1992, J. Mol. Biol. 223:95–104). The third class includes genes for which there is significantly more mRNA in the ΔrpoB leaves than in the leaves of wild-type plants (FIG. 6C). Typical for this class are rpl33 and rpl18 (ribosomal protein genes), accD (encoding a subunit of the acetyl-CoA carboxylase; Sasaki et al., 1993 Plant Physiol. 108:445–449) and ORF2280 (putative ATPase with unknown function; Wolfe 1994, Curr. Genet. 25:379–383). Two additional genes of this class, ndhB (respiratory chain NADH dehydrogenase homologue; Matsubayashi et al., 1987, supra) and clpP (encoding the proteolytic subunit of the Clp ATP-dependent protease; Maurizi et al., 1990 J. Biol. Chem. 265:12546–12552; Gray et al., 1990 Plant Mol. Biol. 15:947–950) form a subgroup of this class which demonstrate significant levels of mRNA in wild-type leaves.

The atpB and atpI ATP synthase genes have both NEP and PEP promoters.

Figure 7:
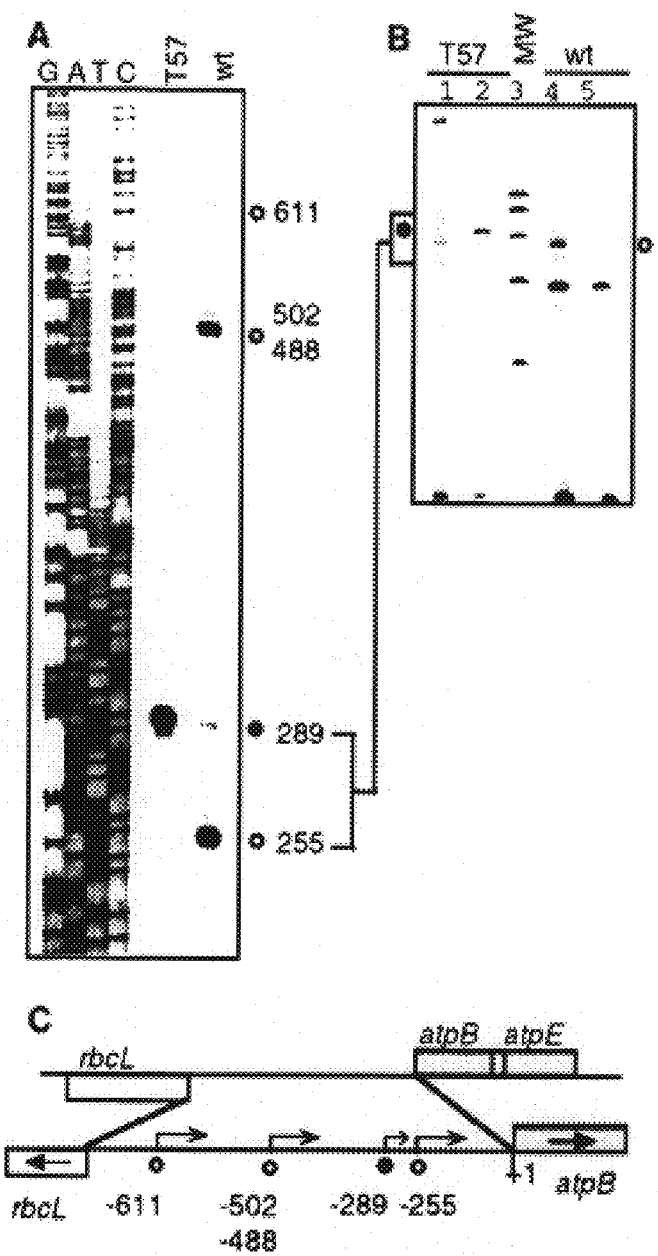
FIG. 7. Mapping atpB transcription initiation sites in wild-type and ΔrpoB tobacco leaves. (A) Primer extension analysis. End-labeled primer extension products from wild-type (wt) and ΔrpoB (T57) samples were run alongside the homologous sequence obtained by using the same primer. Numbers alongside the sequence refer to the distance from the ATG translation initiation codon. Primary transcripts from NEP and PEP promoters are marked by filled and open circles, respectively. (B) In vitro capping and RNase protection assay to identify primary transcript 5' ends. Lanes were loaded with ΔrpoB (T57; 1, 2) and wild-type (wt; 4,5) RNA samples with (2,4) and without (1,5) protecting complementary antisense RNA. Molecular weight (MW) markers (100, 200, 300, 400, and 500 nucleotides) were loaded in lane 3. The transcript 5' end in (A) corresponds to the protected fragment size in brackets: −254 (277 nt), −289 (311). Note artifact slightly below the 200 nt marker which is present in the unprotected RNA samples. (C) Physical map of the atpB—rbcL intergenic region. Map position of the primary transcript 5' ends for the atpB NEP and PEP promoters are marked as in (A).
Figure 8:
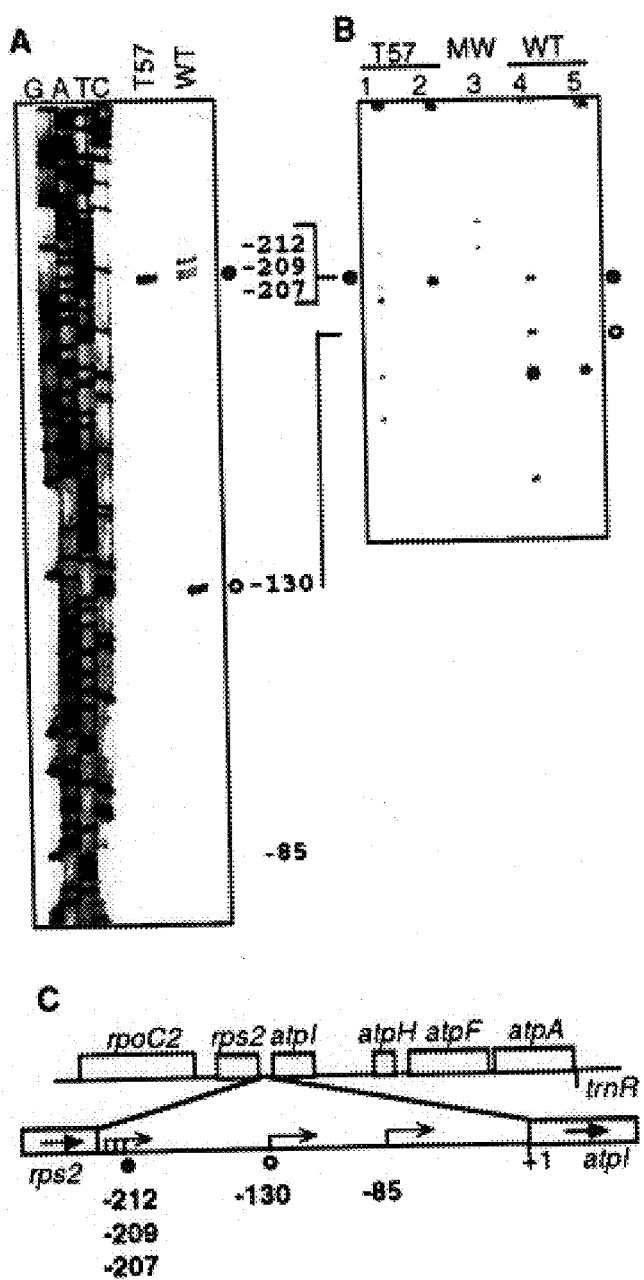
FIG. 8. Mapping atpI transcription initiation sites in wild-type and ΔrpoB tobacco leaves. (A) Primer extension analysis. End-labeled primer extension products from wild-type (wt) and ΔrpoB (T57) samples were run alongside the homologous sequence obtained by using the same primer. Numbers alongside the sequence refer to the distance from the ATG translation initiation codon. Primary transcripts from NEP and PEP promoters are marked by filled and open circles, respectively. (B) In vitro capping and RNase protection assay to identify primary transcript 5' ends. Lanes were loaded with ΔrpoB (T57; 1, 2) and wild-type (wt; 4,5) RNA samples with (2,4) and without (1,5) protecting complementary antisense RNA. Molecular weight (MW) markers (100, 200, 300, 400, and 500 nucleotides) were loaded in lane 3. The transcript 5' end in (A) corresponds to the protected fragment size in brackets: −130 (235 nt), −207, 209, 212 (303, 305, 309; not resolved). Note artifact slightly below the 200 nt marker which is present in the unprotected RNA samples. (C) Physical map of the rps2 —atpI intergenic region. Map position of the primary transcript 5' ends for the atpI NEP and PEP promoters are marked as in (A).

The RNA gel blot analysis identified a number of genes and operons for which high transcript levels are maintained in ΔrpoB leaves. To identify additional NEP promoters, the 5'-end of several transcripts has been mapped by primer extension analysis. 5' ends may be those of primary transcripts identifying a promoter, or generated by RNA processing. Since primary plastid transcripts retain triphosphate groups at their 5' ends, specific [$^{32}$P]GMP transfer to these RNA molecules by the enzyme guanylyltransferase allowed accurate discrimination between primary transcripts and processed ends. For the tobacco atpB operon, transcript 5'-ends have been identified by Orozco et al. (1990 Curr. Genet. 17:65–71.) at nucleotide positions −611, −502, −488, −289 and −255 upstream of the translation initiation codon (FIG. 7C). The 5' ends are numbered relative to the translation initiation codon (ATG) when the nucleotide directly upstream of A is at position −1. Primer extension analysis identified each of these 5'-ends in our wild-type plants (FIG. 7A). In the ΔrpoB sample only the −289 RNA species was present, the 5' end of which was a substrate for guanylyltransferase (FIG. 7B). Therefore, the −289 RNA is transcribed from a NEP promoter, PatpB-289. Interestingly, the −289 transcript is present in the wild-type leaves, although it is less abundant than in the ΔrpoB plants. The −255, −488 and −611 transcripts are absent in the ΔrpoB plants (FIG. 7A). DNA fragments containing these promoters (but not PatpB-289) are recognized by the E. coli RNA polymerase (Orozco et al., 1990, supra), and are transcribed by PEP in plastids. The atpA operon includes the atpI,-atpH-atpF-atpA genes (FIG. 8C). In wild-type tobacco leaves, mRNA 5' ends have been mapped to three regions upstream of atpI,: the −209 region, with 5' ends mapping to nucleotides −212, −209 and −207, and 5'-ends at nucleotides −130 and −85. In ΔrpoB leaves only the −207 transcript is detectable (FIG. 8A). This transcript could be capped in the ΔrpoB RNA sample (FIG. 8B), therefore it is transcribed from a NEP promoter. A signal at this position was also obtained in the in vitro capping reaction of wild-type RNA samples. The −209 and −212 transcripts may be due to the activity of an overlapping PEP promoter, or formation of multiple transcripts from the NEP promoter in wild-type plants. The −130 transcript which is present only in wild-type leaf RNA could also be capped (FIGS. 8A, 8B). Since there are sequences similar to −10/−35 elements at the correct spacing upstream of this 5'-end, it is transcribed by the PEP polymerase.

A clpP NEP promoter is highly expressed in chloroplasts.

Figure 9:
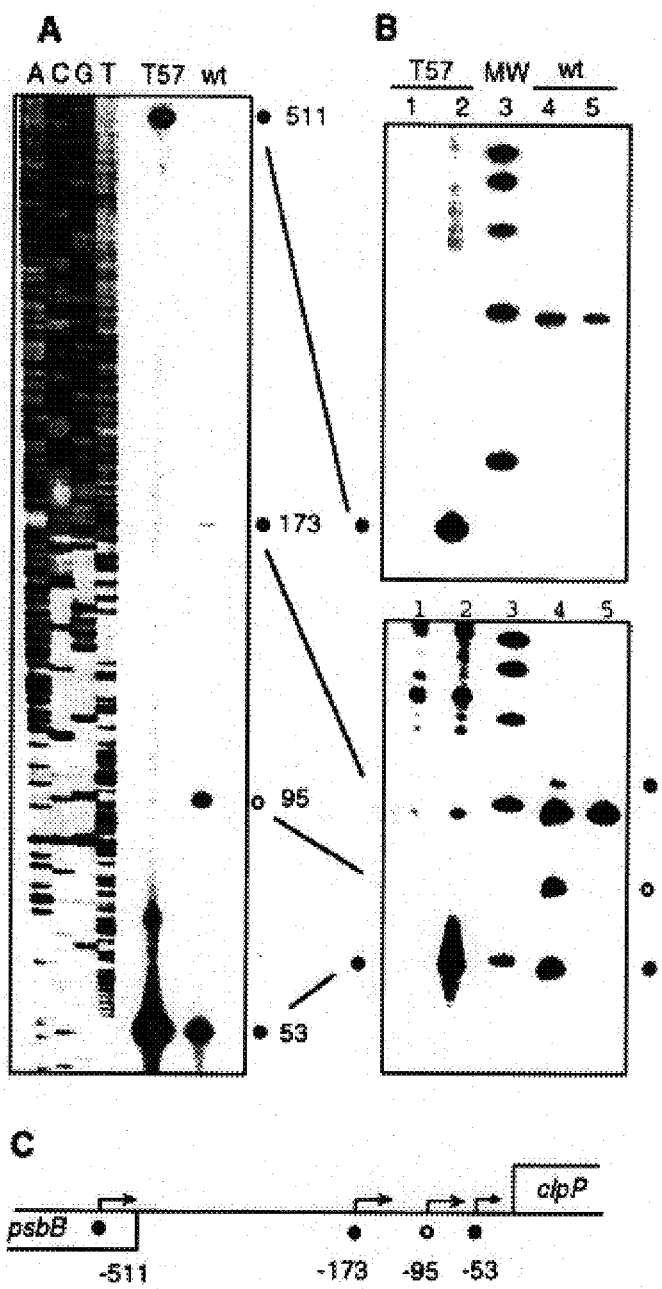
FIG. 9. Mapping clpP transcription initiation sites in wild-type and ΔrpoB tobacco leaves. (A) Primer extension analysis. End-labeled primer extension products from wild-type (wt) and ΔrpoB (T57) samples were run alongside the homologous sequence obtained by using the same primer. Numbers alongside the sequence refer to the distance from the ATG translation initiation codon. Primary transcripts from NEP and PEP promoters are marked by filled and open circles, respectively. (B) In vitro capping and RNase protection assay to identify primary transcript 5' ends. Lanes were loaded with ΔrpoB (T57; 1, 2) and wild-type (wt; 4,5) RNA samples with (2,4) and without (1,5) protecting complementary antisense RNA. Molecular weight (MW) markers (100, 200, 300, 400, and 500 nucleotides) were loaded in lane 3. The transcript 5' end in (A) correspond to the protected fragment size in brackets: −53 (96 nt), −95 (138 nt), −173 (216 nt) and −511 (69 nt). Note artifact slightly below the 200 nt marker which is present in the unprotected RNA samples. (C) Physical map of the clpP—psbB intergenic region. Map position of the primary transcript 5' ends for the clpP NEP and PEP promoters are marked as in (A).

The clpP protease subunit gene also belongs to the class which has both NEP and PEP promoters. Primer extension analysis in the wild-type plants identified RNA 5'-ends at nucleotide positions −53, −95, and −173, while in ΔrpoB plants 5' ends map to the −53, −173, and −511 nucleotide positions (FIG. 9A). In vitro capping reaction verified that each of these are primary transcripts (FIG. 9B). Three of the transcripts derive from NEP promoters. The PclpP-53 promoter is highly expressed in both wild-type-and ΔrpoB plants, thus represents a distinct class of NEP promoters with a potential for high-level expression in different tissue types. The PclpP-53 promoter is well conserved in spinach (Westhoff, 1985 Mol. Gen. Genet. 201:115–123). Additional clpP promoters for NEP are PclpP-173 and PclpP-511. Since the PclpP-511 transcript accumulates only in ΔrpoB plants (FIG. 9A) it is a candidate regulated NEP promoter. Note also, that the PclpP-511 is located within the psbB coding region, and its expression may be affected by the convergent psbB PEP promoter (FIG. 9C).

The only PEP promoter directly upstream of clpP is PclpP-95. RNAs from this promoter accumulate only in wild-type leaves and PclpP-95 has upstream sequences reminiscent of the −10−/−35 conserved elements (not shown).

The accD gene is transcribed exclusively from a NEP promoter.

Figure 10:
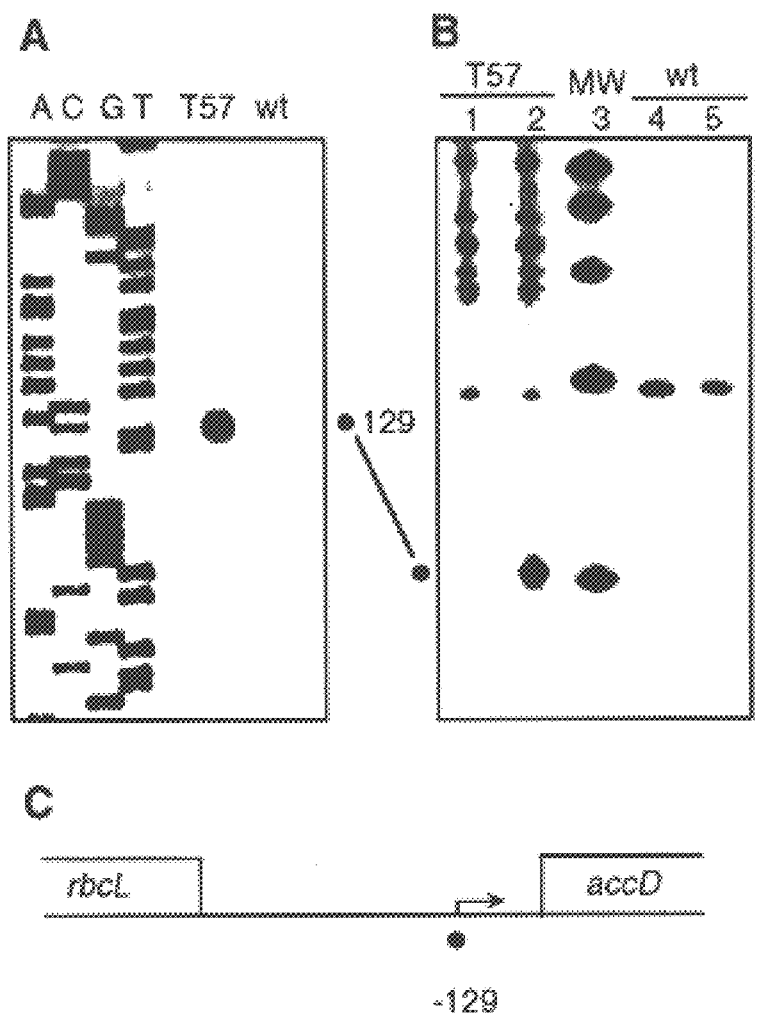
FIG. 10. Mapping accD transcription initiation sites in wild-type and ΔrpoB tobacco leaves. (A) Primer extension analysis. End-labeled primer extension products from wild-type (wt) and ΔrpoB (T57) samples were run alongside the homologous sequence obtained by using the same primer. Numbers alongside the sequence refer to the distance from the ATG translation initiation codon. Primary transcript for the PaccD-129 NEP promoter is marked by a filled circle. (B) In vitro capping and RNAse protection assay to identify primary transcript 5' ends. Lanes were loaded with ΔrpoB (T57; 1, 2) and wild-type (wt; 4,5) RNA samples with (2,4) and without (1,5) protecting complementary antisense RNA. Molecular weight (MW) markers (100, 200, 300, 400, and 500 nucleotides) were loaded in lane 3. The −57 transcript 5' end in (A) corresponds to the protected 103 nt fragment. Note artifact slightly below the 200 nt marker which is present in the unprotected RNA samples. (C) Physical map of the accD—rbcL intergenic region. Map position of the primary transcript 5' end for the PaccD-129 NEP promoter is marked.

For the lipid biosynthetic gene accD, mRNA accumulates to high levels only in ΔrpoB plants. A major transcript initiates at nucleotide position −129 (FIG. 10A), which can be capped in vitro (FIG. 10B). Therefore, this RNA is transcribed from a NEP promoter. Since PaccD-129 does not have a significant activity in the photosynthetically active leaf mesophyll cells, it serves as a candidate for a regulated NEP promoter with a distinct tissue-specific expression pattern.

NEP Promoters Share a Loose Consensus Adjacent to the Transcription Initiation Site.

Figure 11:
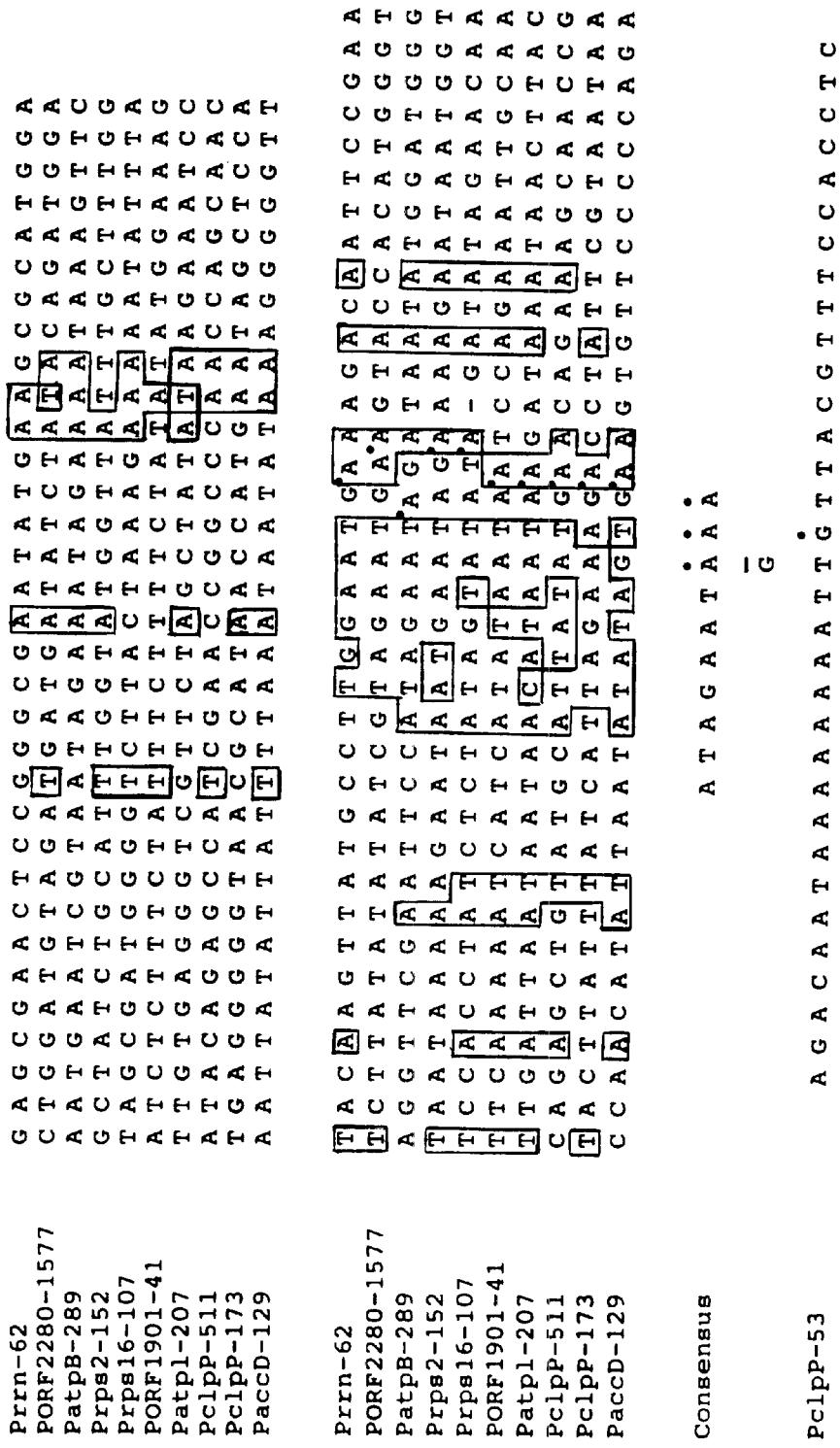
FIG. 11. Alignment of DNA sequences flanking the NEP promoter transcription initiation sites. Nucleotides with more than 6 matches are boxed. Consensus sequence adjacent to the transcription initiation site is shown below. Position of 5' ends are marked by filled circles. Note, that 5' ends for Prps12-152 and Prps16-107 were not capped and may not be primary transcripts. Prnn-62, SEQ ID NO: 59; PORF2280-1577, SEQ ID NO: 60; PatpB-289, SEQ ID NO: 61; Prps2-152, SEQ ID NO: 62; Prps16-107, SEQ ID NO: 63, PORF1901-41, SEQ ID NO: 64; Patp1-207, SEQ ID NO: 65; PclpP-511, SEQ ID NO: 66; PclpP-173, SEQ ID NO: 67; PaccD-129, SEQ ID NO: 68.

Sequences flanking the transcription initiation sites were aligned to identify conserved NEP promoter elements (FIG. 11). Included in the sequence alignment are nine promoters identified in this study and Prrn-62, the NEP promoter described in Allison et al. (1996, supra). Sequences for PORF2280-1577, and PORF1901-41 for which the 5' ends were shown to be primary transcripts by capping in vitro are also included (data not shown). Both of these promoters are active in ΔrpoB leaves but not in the leaves of wild-type plants. Also included in the sequence alignment are tentative NEP promoters for rps2 and rps16 , for which there is more mRNA in ΔrpoB leaves. The 5' ends of these transcripts were mapped by primer extension analysis. The in vitro capping assay failed due to low abundance of the mRNAs (data not shown). Multiple sequence alignment of the regions immediately flanking the NEP 5' ends identified a loose 10 nucleotide consensus around the transcription initiation site (FIG. 11). Conservation of additional nucleotides upstream and downstream is also apparent. Striking is the lack of sequence conservation between the PclpP-53 and other NEP promoters which is the only NEP promoter highly active in chloroplasts. Given the lack of sequence similarity, this sequence was not included in the alignment. Sequences around-the PclpP-53 transcription initiation site are shown separately at the bottom of FIG. 11.

Figure 12:
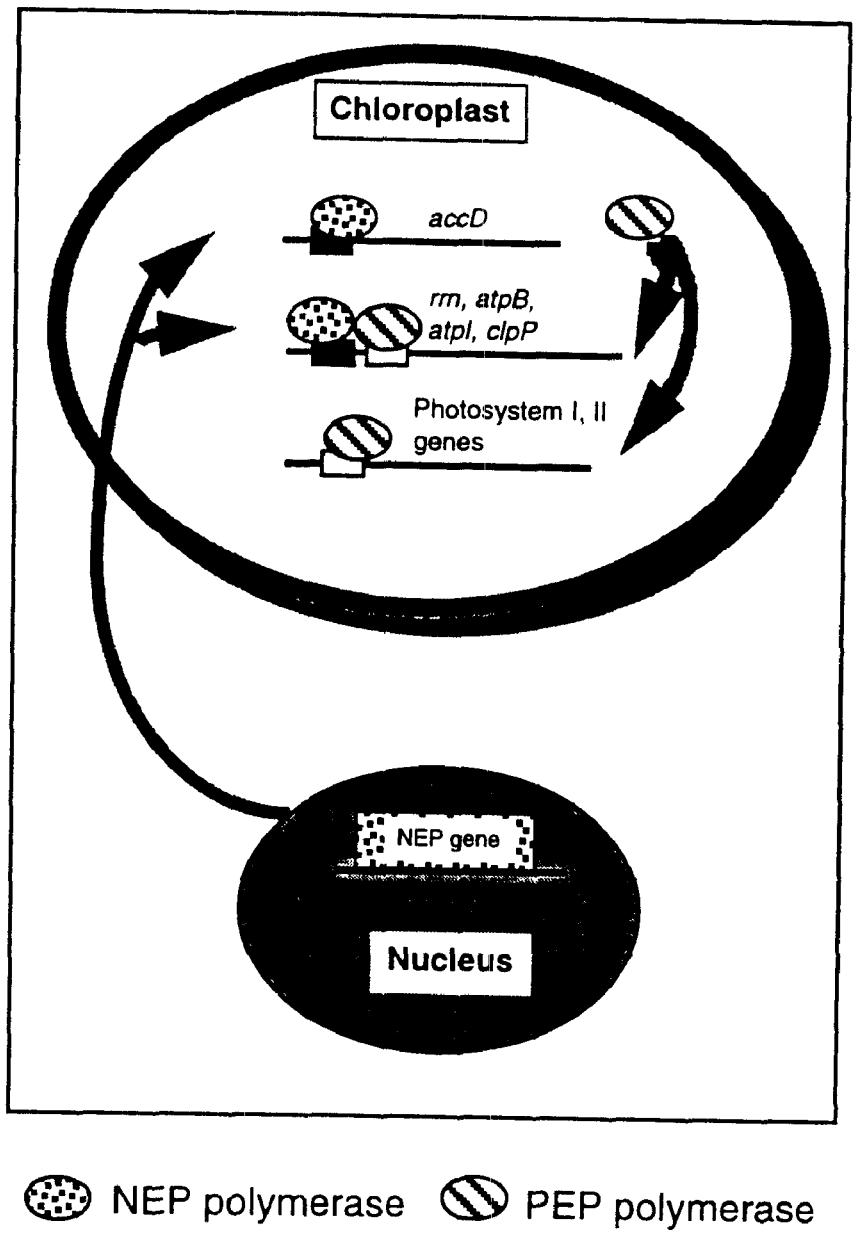
FIG. 12. NEP and PEP polymerases, through recognition of distinct promoters, provide a mechanism for selective transcription of plastid genes. Note that some genes have only PEP promoters (photosystem I and photosystem II), others have both PEP and NEP promoters (most housekeeping genes), or only NEP promoters (accD).

NEP and PEP polymerases, through recognition of distinct promoters, provide a mechanism for selective transcription of plastid genes (FIG. 12). The data provided herein demonstrate that some genes have only PEP promoters or NEP promoters while others have both PEP and NEP regulatory sequences.

EXAMPLE III

NEP Promoters for the Expression of Selectable Marker Genes

For versatility and universal applications, expression of selectable marker genes for plastid transformation is desirable in all tissue types at a high level. Selectable marker genes in the currently utilized plastid transformation vectors are expressed from PEP promoters recognized by the plastid encoded RNA polymerase. The PEP polymerase transcribes photosynthetic genes and some of the housekeeping genes, therefore appears to be the dominant RNA polymerase in photosynthetically active leaf tissues. Efficient plastid transformation has been achieved in tobacco based on chloroplasts transformation in leaf cells. However, plant regeneration is not feasible, or is not practical from the leaves of most agronomically important cereal crops, including maize, rice, wheat and in cotton. In these crops, transgenic plants are typically obtained by transforming embryogenic tissue culture cells or seedling tissue. Given that these tissues are non-photosynthetic, expression of marker genes by NEP promoters which are active in non-green tissues appears to be particularly advantageous, and will facilitate transformation of plastids in all non-photosynthetic tissue types.

A particularly suitable promoter to drive the expression of marker genes is the PclpP-53 promoter. This promoter is highly expressed in the proplastids of ΔrpoB plants, therefore it may also be highly expressed in the proplastids of embryogenic cell cultures which yield transgenic cereal plants. Marker genes expressed from these promoters will also be suitable to select plastid transformants in bombarded leaf cultures, since this promoter was found to be active in chloroplasts. Marker genes expressed from promoters such as the PclpP-53 promoter will have wide application to obtain transformed plastids.

Figure 13:
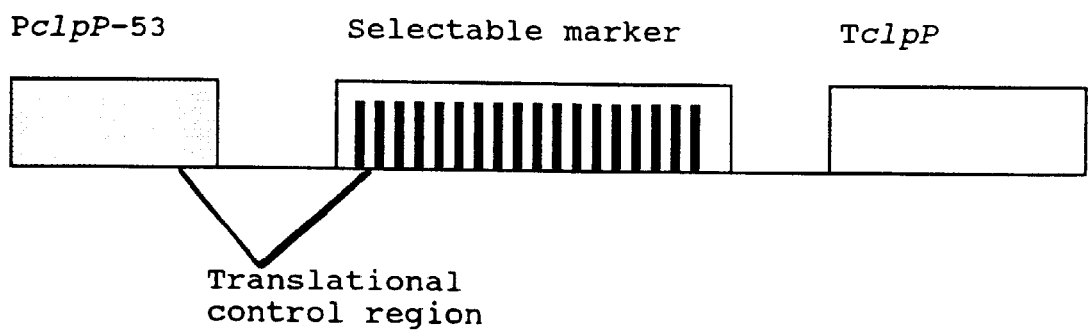
FIG. 13. A schematic diagram of a chimeric plastid gene expressed from a NEP promoter.

The selectable marker genes will be constructed using the principles outlined in U.S. Pat. No. 5,451,513 and pending U.S. application Ser. No. 08/189,256, the subject matter of which is incorporated by reference herein. A transforming DNA construct is illustrated in FIG. 13. More specifically, the PclpP-53 promoter will be cloned upstream of a DNA segment encoding a plastid-selectable marker. Signals for translation will be provided by incorporating suitable DNA sequences between the promoter fragment and the selectable marker coding region. 3' untranslated segments of a plastid gene to provide signals for transcription termination and to stabilize the chimeric mRNA will be cloned downstream of the selectable marker. Utilization of the 3' untranslated region of genes expressed from NEP promoters is preferred since the requirements for transcription termination for the NEP and PEP polymerases may be different.

PclpP-53 is a particularly strong NEP promoter. However, plants with transformed plastids may be obtained with weak promoters as well. There are several examples for such weak NEP promoters in the preceding examples, for example PclpP-173.

Expression of Tissue Specific Plastid Transgenes Driven by NEP Promoters

Tissue specific expression of plastid transgenes is desirable in many applications. Tissue specific expression of a protein that makes the plant tissue repellent or toxic for root nematodes may be desirable in roots. However, expression of the same protein in the leaves would drain the plants resources and may effect utilization of the aerial plant parts. Since most often expressed in non-green tissues, the NEP promoters described in this application, and the promoters expressed from the NEP polymerase in general, are a rich source of tissue-specific promoters for transgene expression.

Several of the NEP promoters, for example PclpP-511, are highly expressed in proplastids of ΔrpoB plants. Proplastids are present in the edible part of cauliflower. Therefore, high level expression of foreign genes in cauliflower is anticipated from this promoter in the edible parts of the plant.

The plastid gene accD encodes a subunit of the prokaryotic acetyl-CoA carboxylase, an enzyme involved in lipid biosynthesis. Interestingly, in wild-type leaves the level of accD mRNA is low while it is high in the proplastids of ΔrpoB plants. This observation suggests that PaccD-129 is active in non-green plastids of tissues actively involved in lipid biosynthesis, such as the plastids of developing seed which is rich in oil.

What is claimed is:

1. A DNA construct for stably transforming plastids of multicellular plants, wherein the construct comprises:
- a transforming DNA having a targeting segment which effects insertion of said transforming DNA into a plastid genome by homologous recombination without disrupting expression of essential genes,
- a selectable marker gene conferring a selectable phenotype to plant cells containing transformed plastids,
- a 3' regulatory region located downstream of said selectable marker gene, wherein the region stabilizes mRNA, and
- a cloning site for insertion of an additional expressible DNA encoding a foreign protein of interest,
- wherein the improvement comprises a 5' promoter element operably linked to said selectable marker gene wherein the promoter element is recognized and transcribed by a plant nuclear encoded plastid RNA polymerase, and wherein the promoter element is selected from the group consisting of Prrn-62 (SEQ ID NO:59), PORF2280-1577 (SEQ ID NO:60), PatpB-289 (SEQ ID NO:61), PORF1901-41 (SEQ ID NO:64), Prbs2-152 (SEQ ID NO:62), Prps16-107 (SEQ ID NO:63), PatpI-207 (SEQ ID NO:65), PclpP-511 (SEQ ID NO:66), PclpP-173 (SEQ ID NO:67), PclpP-53 (SEQ ID NO:70) and PaccD-129 (SEQ ID NO:68).

2. The DNA construct of claim 1, wherein said construct is incorporated into a vector suitable for transformation of plastids.

3. A multicellular plant stably transformed with the DNA construct of claim 2.

4. A multicellular plant stably transformed with the DNA construct of claim 1.

5. A DNA construct for stably transforming the plastids of a plant cell and for expression of at least one additional gene product therein, wherein the construct comprises:
   a) a targeting segment comprising a DNA sequence homologous to a plastid genomic sequence within a plastid to be transformed, said targeting segment enabling homologous recombination with said plastid genomic sequence without disrupting expression of essential genes; and
   b) a selectable marker gene disposed within said targeting segment and being operably linked to a first promoter sequence, said selectable marker gene conferring a selectable phenotype to cells containing plastids expressing said DNA construct; and
   c) an additional DNA segment comprising a transcription unit encoding a protein or a precursor thereof;
   d) a second promoter sequence which is operably linked to said transcription unit, wherein said second promoter sequence is recognized and transcribed by a plant nuclear encoded polymerase, said gene encoding said protein being regulated by said second promoter sequence, and e) at least one 3' regulatory region which functions in plastids to stabilize mRNA transcribed from said DNA construct, wherein said second promoter sequence is selected from the group consisting of Prrn-62 (SEQ ID NO:59), PORF2280-1577 (SEQ ID NO:60), PatpB-289 (SEQ ID NO:61), PORF1901-41 (SEQ ID NO:64), Prps16-107 (SEQ ID NO:63), Prbs2-152 (SEQ ID NO:62), Patpl-207 (SEQ ID NO:65), PclpP-511 (SEQ ID NO:66), PclpP-173 (SEQ ID NO:67), PclpP-53 (SEQ ID NO:70) and PaccD-129 (SEQ ID NO:68).

6. The DNA construct according to claim 5, wherein said first promoter sequence is recognized and transcribed by a plant nuclear encoded plastid polymerase.

7. The DNA construct according to claim 5, wherein said transcription unit encodes a reporter protein.

8. The DNA construct according to claim 5, wherein said construct is incorporated into a vector suitable for transformation of plastids.

9. A method for obtaining a multicellular plant, the plastids of which have been stably transformed by at least one foreign gene of interest, comprising administering to a plant cell a DNA construct comprising:

a) a targeting segment comprising a DNA sequence homologous to a plastid genomic sequence within a plastid to be transformed, said targeting segment enabling homologous recombination with said plastid genomic sequence without disrupting expression of essential genes; and b) a selectable marker gene disposed within said targeting segment, wherein said selectable marker gene confers a selectable phenotype to cells containing plastids expressing said DNA construct, and wherein said selectable marker gene is operably linked to a promoter and further comprises a 3' regulatory region for stabilizing mRNA; and c) a foreign gene of interest, wherein said foreign gene is regulated by a promoter selected from the group consisting of Prrn-62 (SEQ ID NO:59), PORF2280-1577 (SEQ ID NO:60), PatpB-289 (SEQ ID NO:61), PORF1901-41 (SEQ ID NO:64), Prbs2-152 (SEQ ID NO:62), Prps16-107 (SEQ ID NO:63), PatpI-207 (SEQ ID NO:65), PclpP-511 (SEQ ID NO:66), PclpP-173 (SEQ ID NO:67), PclpP-53 (SEQ ID NO:70) and PaccD-129 (SEQ ID NO:68);

selecting for cells which express said selectable phenotype; and regenerating a plant from said cells.

* * * * *

SEQUENCE LISTING

<160> NUMBER OF SEQ ID NOS: 70

<210> SEQ ID NO 1
<211> LENGTH: 15
<212> TYPE: DNA
<213> ORGANISM: Artificial Sequence
<220> FEATURE:
<223> OTHER INFORMATION: PCR Primer

<400> SEQUENCE: 1
cgcttctgta actgg                                                15

<210> SEQ ID NO 2
<211> LENGTH: 16
<212> TYPE: DNA
<213> ORGANISM: Artificial Sequence
<220> FEATURE:
<223> OTHER INFORMATION: PCR Primer

<400> SEQUENCE: 2
tgactgtcaa ctacag                                               16

<210> SEQ ID NO 3
<211> LENGTH: 15
<212> TYPE: DNA
<213> ORGANISM: Artificial Sequence
<220> FEATURE:
<223> OTHER INFORMATION: PCR Primer

<400> SEQUENCE: 3
gttccatcaa tactc                                                15

<210> SEQ ID NO 4
<211> LENGTH: 15
<212> TYPE: DNA
<213> ORGANISM: Artificial Sequence
<220> FEATURE:
<223> OTHER INFORMATION: PCR Primer

<400> SEQUENCE: 4
gccgcggcta aagtt                                                15

<210> SEQ ID NO 5
<211> LENGTH: 15
<212> TYPE: DNA
<213> ORGANISM: Artificial Sequence
<220> FEATURE:
<223> OTHER INFORMATION: PCR Primer

<400> SEQUENCE: 5
tcccacgttc aaggt                                                15

<210> SEQ ID NO 6
<211> LENGTH: 15
<212> TYPE: DNA
<213> ORGANISM: Artificial Sequence
<220> FEATURE:
<223> OTHER INFORMATION: PCR Primer

<400> SEQUENCE: 6
tgagttcgta taggc                                                15

<210> SEQ ID NO 7
<211> LENGTH: 26
<212> TYPE: DNA
<213> ORGANISM: Artificial Sequence
<220> FEATURE:
<223> OTHER INFORMATION: PCR Primer

<400> SEQUENCE: 7
ttcatagttg cattacttat agcttc                                    26

<210> SEQ ID NO 8

```
<211> LENGTH: 30
<212> TYPE: DNA
<213> ORGANISM: Artificial Sequence
<220> FEATURE:
<223> OTHER INFORMATION: PCR Primer

<400> SEQUENCE: 8
acttgcttta gtctctgttt gtggtgacat                                   30

<210> SEQ ID NO 9
<211> LENGTH: 24
<212> TYPE: DNA
<213> ORGANISM: Artificial Sequence
<220> FEATURE:
<223> OTHER INFORMATION: PCR Primer

<400> SEQUENCE: 9
cctctagacc ctaagcccaa tgtg                                         24

<210> SEQ ID NO 10
<211> LENGTH: 28
<212> TYPE: DNA
<213> ORGANISM: Artificial Sequence
<220> FEATURE:
<223> OTHER INFORMATION: PCR Primer

<400> SEQUENCE: 10
ccggtaccga gattcatagt tgcattac                                     28

<210> SEQ ID NO 11
<211> LENGTH: 15
<212> TYPE: DNA
<213> ORGANISM: Artificial Sequence
<220> FEATURE:
<223> OTHER INFORMATION: PCR Primer

<400> SEQUENCE: 11
ggatttaggg gcgaa                                                   15

<210> SEQ ID NO 12
<211> LENGTH: 15
<212> TYPE: DNA
<213> ORGANISM: Artificial Sequence
<220> FEATURE:
<223> OTHER INFORMATION: PCR Primer

<400> SEQUENCE: 12
gtgattttct ctccg                                                   15

<210> SEQ ID NO 13
<211> LENGTH: 15
<212> TYPE: DNA
<213> ORGANISM: Artificial Sequence
<220> FEATURE:
<223> OTHER INFORMATION: PCR Primer

<400> SEQUENCE: 13
agatctgcgc ccgcc                                                   15

<210> SEQ ID NO 14
<211> LENGTH: 15
<212> TYPE: DNA
<213> ORGANISM: Artificial Sequence
<220> FEATURE:
<223> OTHER INFORMATION: PCR Primer

<400> SEQUENCE: 14
```

-continued cctcaccaac gatcc                                                                15

<210> SEQ ID NO 15
<211> LENGTH: 16
<212> TYPE: DNA
<213> ORGANISM: Artificial Sequence
<220> FEATURE:
<223> OTHER INFORMATION: PCR Primer

<400> SEQUENCE: 15
gactttatcg agaaag                                                               16

<210> SEQ ID NO 16
<211> LENGTH: 16
<212> TYPE: DNA
<213> ORGANISM: Artificial Sequence
<220> FEATURE:
<223> OTHER INFORMATION: PCR Primer

<400> SEQUENCE: 16
gagggaatgc tagacg                                                               16

<210> SEQ ID NO 17
<211> LENGTH: 15
<212> TYPE: DNA
<213> ORGANISM: Artificial Sequence
<220> FEATURE:
<223> OTHER INFORMATION: PCR Primer

<400> SEQUENCE: 17
gatatagtgg aagcg                                                                15

<210> SEQ ID NO 18
<211> LENGTH: 15
<212> TYPE: DNA
<213> ORGANISM: Artificial Sequence
<220> FEATURE:
<223> OTHER INFORMATION: PCR Primer

<400> SEQUENCE: 18
gtgaaagaag ttggg                                                                15

<210> SEQ ID NO 19
<211> LENGTH: 15
<212> TYPE: DNA
<213> ORGANISM: Artificial Sequence
<220> FEATURE:
<223> OTHER INFORMATION: PCR Primer

<400> SEQUENCE: 19
cagtcgttgc ttttc                                                                15

<210> SEQ ID NO 20
<211> LENGTH: 15
<212> TYPE: DNA
<213> ORGANISM: Artificial Sequence
<220> FEATURE:
<223> OTHER INFORMATION: PCR Primer

<400> SEQUENCE: 20
ctatcctgag caatt                                                                15

<210> SEQ ID NO 21
<211> LENGTH: 15
<212> TYPE: DNA

```
<213> ORGANISM: Artificial Sequence
<220> FEATURE:
<223> OTHER INFORMATION: PCR Primer

<400> SEQUENCE: 21
ctcggcttct tcctc                                                        15

<210> SEQ ID NO 22
<211> LENGTH: 15
<212> TYPE: DNA
<213> ORGANISM: Artificial Sequence
<220> FEATURE:
<223> OTHER INFORMATION: PCR Primer

<400> SEQUENCE: 22
ctccgttttt acccc                                                        15

<210> SEQ ID NO 23
<211> LENGTH: 15
<212> TYPE: DNA
<213> ORGANISM: Artificial Sequence
<220> FEATURE:
<223> OTHER INFORMATION: PCR Primer

<400> SEQUENCE: 23
gtgactatca agagg                                                        15

<210> SEQ ID NO 24
<211> LENGTH: 16
<212> TYPE: DNA
<213> ORGANISM: Artificial Sequence
<220> FEATURE:
<223> OTHER INFORMATION: PCR Primer

<400> SEQUENCE: 24
gactaacata cgcccg                                                       16

<210> SEQ ID NO 25
<211> LENGTH: 15
<212> TYPE: DNA
<213> ORGANISM: Artificial Sequence
<220> FEATURE:
<223> OTHER INFORMATION: PCR Primer

<400> SEQUENCE: 25
gctcgggagt tcctc                                                        15

<210> SEQ ID NO 26
<211> LENGTH: 15
<212> TYPE: DNA
<213> ORGANISM: Artificial Sequence
<220> FEATURE:
<223> OTHER INFORMATION: PCR Primer

<400> SEQUENCE: 26
tgctcccggt tgttc                                                        15

<210> SEQ ID NO 27
<211> LENGTH: 15
<212> TYPE: DNA
<213> ORGANISM: Artificial Sequence
<220> FEATURE:
<223> OTHER INFORMATION: PCR Primer

<400> SEQUENCE: 27
ggttcgaaga acgtc                                                        15
```

```
<210> SEQ ID NO 28
<211> LENGTH: 15
<212> TYPE: DNA
<213> ORGANISM: Artificial Sequence
<220> FEATURE:
<223> OTHER INFORMATION: PCR Primer

<400> SEQUENCE: 28
ggcccagaaa tacct                                                       15

<210> SEQ ID NO 29
<211> LENGTH: 16
<212> TYPE: DNA
<213> ORGANISM: Artificial Sequence
<220> FEATURE:
<223> OTHER INFORMATION: PCR Primer

<400> SEQUENCE: 29
ttcgttcgcc ggaacc                                                      16

<210> SEQ ID NO 30
<211> LENGTH: 16
<212> TYPE: DNA
<213> ORGANISM: Artificial Sequence
<220> FEATURE:
<223> OTHER INFORMATION: PCR Primer

<400> SEQUENCE: 30
gatctcgatt caagat                                                      16

<210> SEQ ID NO 31
<211> LENGTH: 15
<212> TYPE: DNA
<213> ORGANISM: Artificial Sequence
<220> FEATURE:
<223> OTHER INFORMATION: PCR Primer

<400> SEQUENCE: 31
ggagcacata ttgtg                                                       15

<210> SEQ ID NO 32
<211> LENGTH: 15
<212> TYPE: DNA
<213> ORGANISM: Artificial Sequence
<220> FEATURE:
<223> OTHER INFORMATION: PCR Primer

<400> SEQUENCE: 32
ggattattgc cgatg                                                       15

<210> SEQ ID NO 33
<211> LENGTH: 24
<212> TYPE: DNA
<213> ORGANISM: Artificial Sequence
<220> FEATURE:
<223> OTHER INFORMATION: PCR Primer

<400> SEQUENCE: 33
caatatcagc aatgcagttc atcc                                             24

<210> SEQ ID NO 34
<211> LENGTH: 24
<212> TYPE: DNA
<213> ORGANISM: Artificial Sequence
<220> FEATURE:
```

<223> OTHER INFORMATION: PCR Primer

<400> SEQUENCE: 34
ggaatccttc cagtagtatc ggcc                                        24

<210> SEQ ID NO 35
<211> LENGTH: 25
<212> TYPE: DNA
<213> ORGANISM: Artificial Sequence
<220> FEATURE:
<223> OTHER INFORMATION: PCR Primer

<400> SEQUENCE: 35
cacgaagtat gtgtccggat agtcc                                       25

<210> SEQ ID NO 36
<211> LENGTH: 15
<212> TYPE: DNA
<213> ORGANISM: Artificial Sequence
<220> FEATURE:
<223> OTHER INFORMATION: PCR Primer

<400> SEQUENCE: 36
ggaaagatgt ccgag                                                  15

<210> SEQ ID NO 37
<211> LENGTH: 18
<212> TYPE: DNA
<213> ORGANISM: Artificial Sequence
<220> FEATURE:
<223> OTHER INFORMATION: PCR Primer

<400> SEQUENCE: 37
gttcactaat aaatcgac                                               18

<210> SEQ ID NO 38
<211> LENGTH: 29
<212> TYPE: DNA
<213> ORGANISM: Artificial Sequence
<220> FEATURE:
<223> OTHER INFORMATION: PCR Primer

<400> SEQUENCE: 38
ccgagctctt atttcctatc agactaagc                                   29

<210> SEQ ID NO 39
<211> LENGTH: 27
<212> TYPE: DNA
<213> ORGANISM: Artificial Sequence
<220> FEATURE:
<223> OTHER INFORMATION: PCR Primer

<400> SEQUENCE: 39
ccccagaacc agaagtagta ggattga                                     27

<210> SEQ ID NO 40
<211> LENGTH: 25
<212> TYPE: DNA
<213> ORGANISM: Artificial Sequence
<220> FEATURE:
<223> OTHER INFORMATION: PCR Primer

<400> SEQUENCE: 40
gtattgatgg aacatgatag aacat                                       25

```
<210> SEQ ID NO 41
<211> LENGTH: 26
<212> TYPE: DNA
<213> ORGANISM: Artificial Sequence
<220> FEATURE:
<223> OTHER INFORMATION: PCR Primer

<400> SEQUENCE: 41
gggacttttg gaacaccaat aggcat                                          26

<210> SEQ ID NO 42
<211> LENGTH: 24
<212> TYPE: DNA
<213> ORGANISM: Artificial Sequence
<220> FEATURE:
<223> OTHER INFORMATION: PCR Primer

<400> SEQUENCE: 42
gggagctcca tgggtttgcc ttgg                                            24

<210> SEQ ID NO 43
<211> LENGTH: 27
<212> TYPE: DNA
<213> ORGANISM: Artificial Sequence
<220> FEATURE:
<223> OTHER INFORMATION: PCR Primer

<400> SEQUENCE: 43
cttcatgcat aaggatacta gattacc                                         27

<210> SEQ ID NO 44
<211> LENGTH: 27
<212> TYPE: DNA
<213> ORGANISM: Artificial Sequence
<220> FEATURE:
<223> OTHER INFORMATION: PCR Primer

<400> SEQUENCE: 44
gggagctcta catgaagaac ataagcc                                         27

<210> SEQ ID NO 45
<211> LENGTH: 25
<212> TYPE: DNA
<213> ORGANISM: Artificial Sequence
<220> FEATURE:
<223> OTHER INFORMATION: PCR Primer

<400> SEQUENCE: 45
ccaatatctt cttgtcattt ctctc                                           25

<210> SEQ ID NO 46
<211> LENGTH: 26
<212> TYPE: DNA
<213> ORGANISM: Artificial Sequence
<220> FEATURE:
<223> OTHER INFORMATION: PCR Primer

<400> SEQUENCE: 46
catcgtttca aacgaagttt taccat                                          26

<210> SEQ ID NO 47
<211> LENGTH: 24
<212> TYPE: DNA
<213> ORGANISM: Artificial Sequence
<220> FEATURE:
<223> OTHER INFORMATION: PCR Primer
```

-continued

```
<400> SEQUENCE: 47
ccggtaccat aggagaagcc gccc                                    24

<210> SEQ ID NO 48
<211> LENGTH: 27
<212> TYPE: DNA
<213> ORGANISM: Artificial Sequence
<220> FEATURE:
<223> OTHER INFORMATION: PCR Primer

<400> SEQUENCE: 48
ccgagctcgt agtaggattg attctca                                 27

<210> SEQ ID NO 49
<211> LENGTH: 27
<212> TYPE: DNA
<213> ORGANISM: Artificial Sequence
<220> FEATURE:
<223> OTHER INFORMATION: PCR Primer

<400> SEQUENCE: 49
ccggtaccgg agccaattag atacaaa                                 27

<210> SEQ ID NO 50
<211> LENGTH: 24
<212> TYPE: DNA
<213> ORGANISM: Artificial Sequence
<220> FEATURE:
<223> OTHER INFORMATION: PCR Primer

<400> SEQUENCE: 50
ccgagctctg acttggaaac cccc                                    24

<210> SEQ ID NO 51
<211> LENGTH: 25
<212> TYPE: DNA
<213> ORGANISM: Artificial Sequence
<220> FEATURE:
<223> OTHER INFORMATION: PCR Primer

<400> SEQUENCE: 51
ccgaattcta gtattcgcaa tttgt                                   25

<210> SEQ ID NO 52
<211> LENGTH: 24
<212> TYPE: DNA
<213> ORGANISM: Artificial Sequence
<220> FEATURE:
<223> OTHER INFORMATION: PCR Primer

<400> SEQUENCE: 52
gggagctcca ggacttcgga aagg                                    24

<210> SEQ ID NO 53
<211> LENGTH: 22
<212> TYPE: DNA
<213> ORGANISM: Artificial Sequence
<220> FEATURE:
<223> OTHER INFORMATION: PCR Primer

<400> SEQUENCE: 53
ggggtaccaa tacgcaatgg gg                                      22

<210> SEQ ID NO 54
<211> LENGTH: 24
```

```
<212> TYPE: DNA
<213> ORGANISM: Artificial Sequence
<220> FEATURE:
<223> OTHER INFORMATION: PCR Primer

<400> SEQUENCE: 54
ggggtaccgc taattcatac agag                                               24

<210> SEQ ID NO 55
<211> LENGTH: 23
<212> TYPE: DNA
<213> ORGANISM: Artificial Sequence
<220> FEATURE:
<223> OTHER INFORMATION: PCR Primer

<400> SEQUENCE: 55
gggagctccg accacaacga ccg                                                23

<210> SEQ ID NO 56
<211> LENGTH: 25
<212> TYPE: DNA
<213> ORGANISM: Artificial Sequence
<220> FEATURE:
<223> OTHER INFORMATION: PCR Primer

<400> SEQUENCE: 56
ggggtaccct tacatgcctc atttc                                              25

<210> SEQ ID NO 57
<211> LENGTH: 27
<212> TYPE: DNA
<213> ORGANISM: Artificial Sequence
<220> FEATURE:
<223> OTHER INFORMATION: PCR Primer

<400> SEQUENCE: 57
ggggtaccgt gcctaagggc atatcgg                                            27

<210> SEQ ID NO 58
<211> LENGTH: 201
<212> TYPE: DNA
<213> ORGANISM: N. tobacco

<400> SEQUENCE: 58
atttgctccc ccgccgtcgt tcaatgagaa tggataagag gctcgtggga ttgacgtgag         60
ggggcaggga tggctatatt tctgggagcg aactccgggc gaatatgaag cgcatggata        120
caagttatgc cttggaatga aagacaattc cgaatccgct ttgtctacga acaaggaagc        180
tataagtaat gcaactatga a                                                 201

<210> SEQ ID NO 59
<211> LENGTH: 69
<212> TYPE: DNA
<213> ORGANISM: N. tobacco

<400> SEQUENCE: 59
gagcgaactc cgggcgaata tgaagcgcat ggatacaagt tatgccttgg aatgaaagac         60
aattccgaa                                                                69

<210> SEQ ID NO 60
<211> LENGTH: 69
<212> TYPE: DNA
<213> ORGANISM: N. tobacco
```

```
<400> SEQUENCE: 60
ctggatgtag atgatgatat ctatacagat ggatcttata tatatcgtag aatgaagtac    60
cacatgggt                                                            69

<210> SEQ ID NO 61
<211> LENGTH: 69
<212> TYPE: DNA
<213> ORGANISM: N. Tobacco

<400> SEQUENCE: 61
aatgaatcgt aatagaaata gaaataaag ttcaggttcg aattccatag aatagataat     60
atggatggg                                                            69

<210> SEQ ID NO 62
<211> LENGTH: 69
<212> TYPE: DNA
<213> ORGANISM: N. tobacco

<400> SEQUENCE: 62
gctatctgca tttggtatgg ttatttgctt tggtaataaa agaataatg aatagaaaag     60 aataatggt                                                            69

<210> SEQ ID NO 63
<211> LENGTH: 68
<212> TYPE: DNA
<213> ORGANISM: N. tobacco

<400> SEQUENCE: 63
tagcgatggg gtcttactaa agaaaaatat ttatccacct atctctatag tatatagata    60
tagaacaa                                                             68

<210> SEQ ID NO 64
<211> LENGTH: 69
<212> TYPE: DNA
<213> ORGANISM: N. tobacco

<400> SEQUENCE: 64
atctctttct atttcttttc tatatatgga agttcaaaa atcatcatat aataatccag     60
aaattgcaa                                                            69

<210> SEQ ID NO 65
<211> LENGTH: 69
<212> TYPE: DNA
<213> ORGANISM: N. tobacco

<400> SEQUENCE: 65
ttgtgagggt cgttctagct atataagaaa tccttgatta ataataacat aataagataa    60
ataacttac                                                            69

<210> SEQ ID NO 66
<211> LENGTH: 69
<212> TYPE: DNA
<213> ORGANISM: N. tobacco

<400> SEQUENCE: 66
atacagagcc atcgaaccgg cccaaccagc aaccagagct gtatgcatta tatgaacaga    60
aagcaaccg                                                            69
```

```
<210> SEQ ID NO 67
<211> LENGTH: 69
<212> TYPE: DNA
<213> ORGANISM: N. tobacco

<400> SEQUENCE: 67
tgagggggta acgcataacc atgaatagct ccatacttat ttatcattag aaagacctat    60
tcgtaataa                                                            69

<210> SEQ ID NO 68
<211> LENGTH: 69
<212> TYPE: DNA
<213> ORGANISM: N. tobacco

<400> SEQUENCE: 68
aattatatta ttttaaataa tataaagggg gttccaacat attaatatat agtgaagtgt    60
tcccccaga                                                            69

<210> SEQ ID NO 69
<211> LENGTH: 10
<212> TYPE: DNA
<213> ORGANISM: Artificial Sequence
<220> FEATURE:
<223> OTHER INFORMATION: Consensus Sequence

<400> SEQUENCE: 69
atagaataaa                                                           10

<210> SEQ ID NO 70
<211> LENGTH: 36
<212> TYPE: DNA
<213> ORGANISM: N. tobacco

<400> SEQUENCE: 70
agacaataaa aaaaattgtt acgtttccac ctcaaa                              36
```